(12) United States Patent
Barres et al.

(10) Patent No.: US 8,148,330 B2
(45) Date of Patent: Apr. 3, 2012

(54) MODULATION OF SYNAPTIC MAINTENANCE

(75) Inventors: Ben A. Barres, Stanford, CA (US); Beth A. Stevens, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1426 days.

(21) Appl. No.: 11/636,001

(22) Filed: Dec. 8, 2006

(65) Prior Publication Data

US 2007/0135753 A1 Jun. 14, 2007

Related U.S. Application Data

(60) Provisional application No. 60/749,071, filed on Dec. 9, 2005.

(51) Int. Cl.
*A61K 38/55* (2006.01)
*C07K 17/10* (2006.01)

(52) U.S. Cl. .............. 514/20.3; 606/6; 530/395
(58) Field of Classification Search .............. None
See application file for complete search history.

(56) References Cited

U.S. PATENT DOCUMENTS

| | | |
|---|---|---|
| 2002/0066117 A1 | 5/2002 | Nilsson et al. |
| 2002/0104104 A1 | 8/2002 | Games et al. |
| 2005/0241008 A1 | 10/2005 | Bredesen et al. |

OTHER PUBLICATIONS

Choi, 2003, J Korean Neurol Assoc., 21, 513-520.*
Veerhuis, 1998, Acta Neuropathol, 96, 287-296.*
Yasojima, 1999, Brain Research, 833, 297-301.*
Fonseca; et al., "Absence of C1q Leads to Less Neuropathology in Transgenic Mouse Models of Alzheimer's Disease", The Journal of Neuroscience (2004), 24(29):6457-6465.

* cited by examiner

*Primary Examiner* — Cecilia J Tsang
*Assistant Examiner* — Satyanarayana Gudibande
(74) *Attorney, Agent, or Firm* — Bozicevic, Field & Francis LLP; Elizabeth A. Alcamo

(57) ABSTRACT

C1q is shown to be expressed in neurons, where it acts as a signal for synapse elimination. Methods are provided for protecting or treating an individual suffering from adverse effects of synapse loss. These findings have broad implications for a variety of clinical conditions, including Alzheimer's disease.

1 Claim, 13 Drawing Sheets
(12 of 13 Drawing Sheet(s) Filed in Color)

A

| | Signal level | | Signal level | | Fold-change |
|---|---|---|---|---|---|
| | -Astros | | +Astros | | |
| C1qA | 213.4 | A | 823.8 | P | 4.2 |
| C1qB | -109 | A | 1309.5 | P | ~26.9 |
| C1qB | -72.9 | A | 512.9 | P | ~11.0 |
| C1qC | -135.8 | A | 614.8 | P | ~16.6 |

B

C

A

B

SEQUENCE LISTING

<160> NUMBER OF SEQ ID NOS: 9

<210> SEQ ID NO 1
<211> LENGTH: 39
<212> TYPE: DNA
<213> ORGANISM: Artificial Sequence
<220> FEATURE:
<223> OTHER INFORMATION: Synthetic primer

<400> SEQUENCE: 1
ggccagtgaa ttgtaatacg actcactata gggaggcgg        39

<210> SEQ ID NO 2
<211> LENGTH: 29
<212> TYPE: DNA
<213> ORGANISM: Artificial Sequence
<220> FEATURE:
<223> OTHER INFORMATION: Synthetic primer

<400> SEQUENCE: 2
cggaattccc ttctctgccc tgaggacgg        29

<210> SEQ ID NO 3
<211> LENGTH: 29
<212> TYPE: DNA
<213> ORGANISM: Artificial Sequence
<220> FEATURE:
<223> OTHER INFORMATION: Synthetic primer

<400> SEQUENCE: 3 cgggatccctt tctgcatgcg gtctcggtc        29

<210> SEQ ID NO 4
<211> LENGTH: 29
<212> TYPE: DNA
<213> ORGANISM: Artificial Sequence
<220> FEATURE:
<223> OTHER INFORMATION: Synthetic primer

<400> SEQUENCE: 4
cggaattcga caaggtcctc accaaccag        29

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
cgggatccgg ggtccttctc gatcc        25

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccgggggagc caggtgtgga g        21

<210> SEQ ID NO 7
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 7
gcacaggttg gccgtatgcg                                              20

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ggtcttactc cttggaggcc atgt                                         24

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gaccccttca ttgacctcaa ctaca                                        25
```

MODULATION OF SYNAPTIC MAINTENANCE

FEDERALLY-SPONSORED RESEARCH OR DEVELOPMENT

This invention was made with Government support under contract DA015043 awarded by the National Institutes of Health. The Government has certain rights in this invention.

BACKGROUND OF THE INVENTION

The formation of precise neuronal circuits during development is a highly regulated and dynamic process. Excess numbers of synapses are first generated to establish the initial wiring pattern of the brain, but the formation of mature, precise neuronal circuits requires the selective elimination and pruning of specific synapses. Neuronal activity plays a critical role in this refinement phase, but surprisingly, the specific molecular mechanisms underlying synapse elimination remain a mystery. In the adult brain, synapse loss often occurs long before the pathology and clinical symptoms in many neurodegenerative diseases. Identification of the instructive molecule(s) that mark synapses for elimination during development could also provide important clinical insight about therapeutic targets for devastating diseases such as Alzheimer's.

Synapses are specialized cell adhesions that are the fundamental functional units of the nervous system, and they are generated during development with amazing precision and fidelity. During synaptogenesis, synapses form, mature, and stabilize and are also eliminated by a process that requires intimate communication between pre- and postsynaptic partners. In addition, there may be environmental determinants that help to control the timing, location, and number of synapses.

Synapses occur between neuron and neuron and, in the periphery, between neuron and effector cell, e.g. muscle. Functional contact between two neurons may occur between axon and cell body, axon and dendrite, cell body and cell body, or dendrite and dendrite. It is this functional contact that allows neurotransmission. Many neurologic and psychiatric diseases are caused by pathologic overactivity or underactivity of neurotransmission; and many drugs can modify neurotransmission, for examples hallucinogens and antipsychotic drugs.

Glial cells associated with synapses, either astrocytes in the CNS or Schwann cells in the PNS, are thought to provide synaptic insulation by preventing neurotransmitter spillover to neighboring synapses and they also help to terminate neurotransmitter action. In addition, glial cells supply synapses with energetic substrates. The possible requirement of glia for synapse formation is suggested by the temporal association of synaptic development with glial development: although most neurons are born prior to the birth of most glia, the vast majority of synapses develop during the first few weeks of postnatal life, during the period of glial generation. For example, axons of retinal ganglion cells (RGCs) reach their target in the superior colliculus by embryonic day 16, but they do not form many synapses until the second postnatal week, coinciding with glial generation. Therefore the formation of many or most synapses is delayed until glial cells are present.

During development, competition between axons causes permanent removal of synaptic connections. The synapses to be eliminated become progressively weaker, are eliminated, and then the competing axon extends axonal processes to occupy those sites. These findings have lead to a simple model in which synaptic transmission produces two postsynaptic signals: a short range protective signal and a longer range elimination (punishment) signal. Functionally weak synapses are not protected from the elimination signal of neighboring stronger synapses, resulting in the disappearance of postsynaptic receptors and withdrawal of the axon. This withdrawal then provides the opportunity for the stronger axon to expand into the vacated territory. The identity of the punishment and protection signals have heretofore been unknown.

Shortly after birth, neonatal brains undergo a period of intense synaptic proliferation to levels far greater than those seen in adult brains. Later in infancy there is a spontaneous, normal period of synaptic pruning or reduction. In rhesus monkeys the synaptic density (i.e., the number of synapses per unit of brain tissue volume) peaks at 2 to 4 months of age and then gradually declines until about age 3 years, where it remains at adult levels. The proliferation and pruning appear to occur uniformly throughout the rhesus cortex.

Data on human brains suggest that these programmed fluctuations in synaptic density also occur, but they vary by brain region. Synaptogenesis in the visual cortex, for example, begins its rapid growth at about age 2 months, peaks at 8 to 10 months, and then declines gradually until about age 10 years. By contrast, synaptogenesis in the frontal cortex begins and peaks later, and pruning is not complete until adolescence. Interpretation of these findings about synaptic density counts is further complicated because synaptogenesis and pruning may occur at different rates in different structures within the same brain region or even for a particular group of neurons in different parts of their dendritic fields.

Two phenomena thought to be related to this process of synaptogenesis and pruning are those of so-called "critical periods" and neural plasticity, both of which have been studied extensively over the past 30 years. Deprivation of adequate sensory or motor input during particular times in a specific brain system's development (i.e., the critical period) can lead to impairments in that system's functioning, both at that time and in the future.

It is now thought that the need for appropriate sensory input is greatest during a brain system's period of rapid synaptogenesis and that experiential input helps shape the particular synaptic connections that are formed and also which ones are eliminated. This process corresponds to the "experience-expectant" type of neural plasticity that is tied to the brain's developmental timetable. By contrast, "experience-dependent" plasticity allows incorporation of useful but idiosyncratic information throughout life. The onset of critical periods and their durations vary widely over the different neural systems in the brain. At present, it is not known whether there are critical periods during which particular types of stimulation are needed and after which plasticity is greatly reduced. Nor is it known whether neuronal plasticity responsiveness is present in discreet, sensitive periods versus demonstrating more gradual decrease over time.

Although there are varied etiologies among neurodegenerative diseases, one cellular commonality which exists among all neurons is the synapse. Degeneration of functional synapses is of crucial importance to understanding the primary mechanisms of overall neurodegeneration. Evidence suggests that synapse loss precedes neuron loss, e.g. in early Alzheimer's Disease (AD). Several studies have correlated synapse loss with clinically defined neurological impairment. For example, statistical analysis has shown that synapse loss is more closely correlated with cognitive impairment in AD than are plaques and tangles. Moreover, a variety of proteins found in pathological hallmarks of neurodegenerative diseases are synaptic proteins or cleavage products of synaptic proteins. These include APP, amyloid precursor protein, alpha-synuclein, the precursor of NAC peptide found in Lewy bodies in Parkinson's Disease, and PrP.

These observations emphasize that synapse loss is a central event in neurodegeneration and that synaptic proteins have been involved in the neuropathology of disease. Despite this fundamental understanding, there has been little systematic study of synapse loss or the role of synaptic proteins associated with pathology. The modulation of synapse maintenance and loss is of great interest for the treatment of a variety of nervous system disorders. The present invention addresses this issue.

SUMMARY OF THE INVENTION

Methods are provided for the modulation of synaptic development, including synapse elimination. It has been found that specific complement proteins are expressed by neurons, and are involved in the pathway for elimination of synapses. Agents that inhibit complement activation, including agents that block specific components, such C1q, can prevent synapse elimination from neurons. Neurons affected by synapse loss may be central nervous system neurons, or peripheral nervous system neurons.

In one embodiment of the invention, methods are provided for screening candidate agents for the ability to modulate synaptic development, including synapse elimination. In one embodiment of the invention the neurons are neurons in the central nervous system. In another embodiment, the neurons are peripheral nervous system neurons. Screening methods are also provided for determining signaling molecules involved in the synapse elimination pathway, e.g. molecules expressed by astrocytes, including immature astrocytes.

Methods are provided for protecting or treating an individual suffering from adverse effects of synapse loss. These findings have broad implications for a variety of clinical conditions, including neurodegenerative conditions involving synaptic loss, which conditions may include Alzheimer's disease; amyotrophic lateral sclerosis; multiple sclerosis, glaucoma, myotonic dystrophy, Down syndrome; Parkinson's disease, Huntington's disease; and the like. The loss of synapses is inhibited by contacting neurons with agents that block complement, including specific components, such as C1q.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
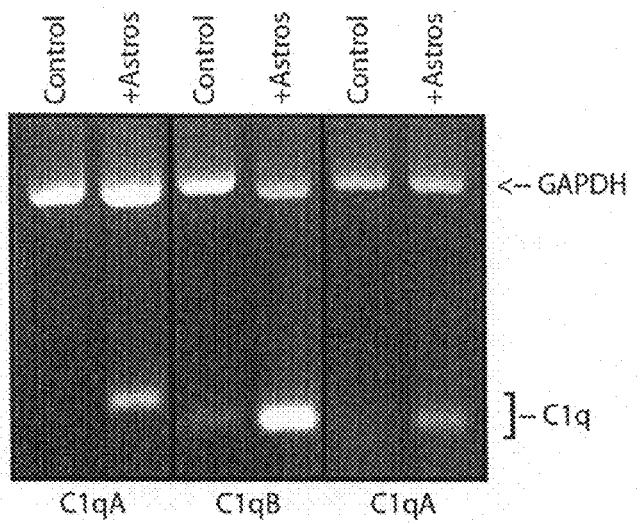
FIGS. 1A-1C. Astrocytes up-regulate C1q expression in neurons. A. Gene chip analysis (Affymetrix) of RNA prepared from purified RGCs showed C1q was the only gene significantly (10-30 fold) up-regulated by astrocytes. B. RT-PCR validated that all three chains (A, B, C) of C1q were significantly up-regulated in RGCs upon exposure to astrocytes. C. C1q is highly expressed in retinal ganglion cells in vivo. RT-PCR analysis of mRNA isolated from RGCs that were acutely isolated from P5 retina (left lane), and perfused postnatal mouse retina.
Figure 1:
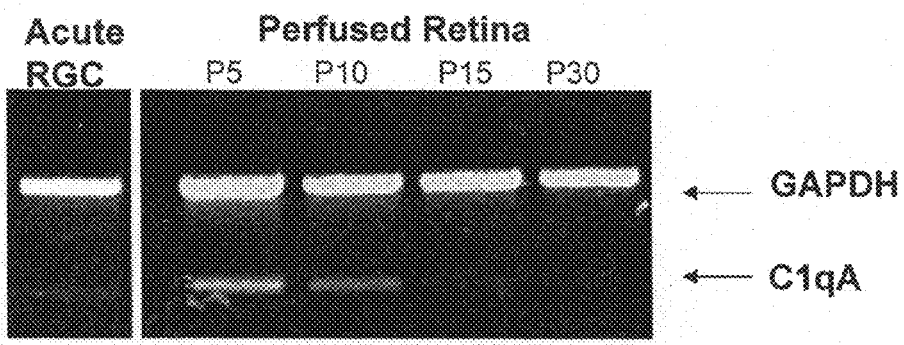

Methods are provided for protecting or treating an individual suffering from adverse effects of synapse loss. It is shown herein that immature astrocytes in normal development produce a signal that induces neurons to express specific complement proteins, thus enabling a developmental window during which synapse elimination occurs. Expression of these proteins in development mirrors the period of developmental synaptogenesis, being off in embryonic brain and adult brain but on at high levels in postnatal brain.

These findings have broad implications for a variety of clinical conditions, particularly neurodegenerative conditions where synapse loss is involved. Synapse loss is inhibited by contacting neurons with inhibitors or antagonists of the complement pathway. For example, inhibitors can block activation of the complement cascade, can block the expression of specific complement proteins in neurons, can interfere with signaling molecules that induce complement activation, can upregulate expression of complement inhibitors in neurons, and otherwise interfere with the role of complement in synapse loss. The ability to prevent synapse loss, e.g. in adult brains, has important implications for maintaining normal neuronal function in a variety of neurodegenerative conditions.

DEFINITIONS

Synapse loss. Synapses are asymmetric communication junctions formed between two neurons, or, at the neuromuscular junction (NMJ) between a neuron and a muscle cell. Chemical synapses enable cell-to-cell communication via secretion of neurotransmitters, whereas in electrical synapses signals are transmitted through gap junctions, specialized intercellular channels that permit ionic current flow. In addition to ions, other molecules that modulate synaptic function (such as ATP and second messenger molecules) can diffuse through gap junctional pores. At the mature NMJ, pre- and postsynaptic membranes are separated by a synaptic cleft containing extracellular proteins that form the basal lamina. Synaptic vesicles are clustered at the presynaptic release site, transmitter receptors are clustered in junctional folds at the postsynaptic membrane, and glial processes surround the nerve terminal.

Synaptogenesis is a dynamic process. During development, more synapses are established than ultimately will be retained. Therefore, the elimination of excess synaptic inputs is a critical step in synaptic circuit maturation. Synapse elimination is a competitive process that involves interactions between pre- and postsynaptic partners. In the CNS, as with the NMJ, a developmental, activity-dependent remodeling of synaptic circuits takes place by a process that may involve the selective stabilization of coactive inputs and the elimination of inputs with uncorrelated activity. The anatomical refinement of synaptic circuits occurs at the level of individual axons and dendrites by a dynamic process that involves rapid elimination of synapses. As axons branch and remodel, synapses form and dismantle with synapse elimination occurring rapidly.

In addition to the normal developmental loss, synapse loss is an early pathological event common to many neurodegenerative disorders, and is the best correlate to the cognitive impairment. Studies in the brains of patients with pre-clinical Alzheimer's disease (AD), as well as in transgenic animal models have shown that synaptic damage occurs early in disease progression. This early disruption of synaptic connections in the brain results in neuronal dysfunction that, in turn, leads to the characteristic symptoms of dementia and/or motor impairment observed in several neurodegenerative disorders.

Several molecules involved in AD and other neurodegenerative disorders play an important role in synaptic function. For example, AβPP has a preferential localization at central and peripheral synaptic sites. In transgenic mice, abnormal expression of mutant forms of AβPP results not only in amyloid deposition, but also in widespread synaptic damage. This synaptic pathology occurs early and is associated with levels of soluble Aβ1-42 rather than with plaque formation. Other neurodegenerative diseases where gene products have been shown to be closely associated with synaptic complexes include Huntington's disease (HD) and myotonic dystrophy (DM). Huntingtin is a membrane-bound protein with a distribution very similar to that of synaptic vesicle protein synaptophysin. Studies in human brain detected htt in perikarya of some neurons, neuropil, varicosities and as punctate staining likely to be nerve endings. The serine/threonine kinase (DMK), which is the gene product of the DM gene, has been found to localize post-synaptically at the neuromuscular junction of skeletal muscle and at intercalated discs of cardiac tissue. DMK was also found at synaptic sites in the cerebellum, hippocampus, midbrain and medulla.

Inhibiting synapse loss results maintenance or reduced loss of synapses, where a decrease would otherwise occur. By "modulation" of synapse loss as used herein, it is meant that the number of synapses lost is either enhanced or suppressed as required in the specific situation. As used herein, the term "modulator of synapse loss" refers to an agent that is able to alter synapse loss. Modulators include, but are not limited to, both "activators" and "inhibitors". An "activator" or "agonist" is a substance that enhances synapse loss. Conversely, an "inhibitor" or "antagonist" decreases synapse loss. The reduction may be complete or partial. As used herein, modulators include, without limitation, C1q antagonists and agonists.

Agonists and antagonists may include proteins, nucleic acids, carbohydrates, antibodies, or any other molecules that decrease the effect of a protein. The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

Complement. Complement is a system of plasma proteins that interacts with the cell surfaces of pathogens or cells to mark them for destruction by phagocytes. The complement system is made up of a large number of distinct plasma proteins, primarily produced by the liver. A number of these proteins are a class of proteases, called zymogens, which are themselves activated by proteolytic cleavage. These zymogens can thus be widely distributed without being active until activated by a local pathogen. The complement system thus is activated through a triggered enzyme cascade.

The classical pathway is activated by the binding of the complement protein C1q directly to the cell surface or to an antibody that is bound to the cell surface. C1q is a large multimeric protein of 460 kDa consisting of 18 polypeptide chains (6 C1q A chains, 6 C1q B chains, and 6 C1q C chains). C1r and C1s complement proteins to bind to the C1q tail region to form the C1 complex. Binding of the C1q complex to the surface of a cell or to the complement binding domain of an antibody Fc region induces a conformational change in C1q that leads to activation of an autocatalytic enzymatic activity in C1r, which then cleaves C1s to generate an active serine protease. Once activated, C1s cleaves C4, etc, leading to the complement cascade sequence. Ultimately this pathway leads to the formation of a membrane attack complex which lyses and kills the affected cell. Normal cells, including neurons, express molecules such as CD59 that protect them from lysis or damage from the membrane attack complex and the C1 inhibitor (C1-INH) which dissociates C1r and C1s from the active C1 complex.

Various complement proteins are expressed by neurons and glial cells in vitro and in vivo. Their function in the brain is unknown. The expression of many of these complement proteins is upregulated by serum or inflammatory cytokines or after brain injury. Astrocytes in culture have been reported to express C1q, C1r, C1s, C4, C2, and C3, as well as the more terminal proteins. Neurons have been reported to express C4 and C3, but only to express C1q after brain injury.

Three pathways have been elucidated through which the complement cascade can be initiated; classical, alternate and lectin Pathways. All three pathways merge through at common intersection, complement C3. C3 is an acute phase reactant. The liver is the main site of synthesis, although small amounts are also produced by activated monocytes and macrophages. A single chain precursor (pro-C3) of approximately 200 kD is found intracellularly; the cDNA shows that it comprises 1,663 amino acids. This is processed by proteolytic cleavage into alpha and beta subunits which in the mature protein are linked by disulfide bonds. Pro-C3 contains a signal peptide of 22 amino acid residues, the beta chain (645 residues) and the alpha chain (992 residues). The 2 chains are joined by 4 arginine residues that are not present in the mature protein.

In the alternate pathway complement C3 undergoes spontaneous cleavage resulting in complement B binding to C3b. Diffusion of the Ba subunit results in an active alternate pathway C3 convertase (C3bBb). C3bBb is stabilized by binding to properdin prior to merging Inhibition of complement. A number of molecules are known that inhibit the activity of complement. In addition to known compounds, suitable inhibitors can be screened by methods described herein. As described above, normal cells can produce proteins that block complement activity, e.g. CD59, C1 inhibitor, etc. In some embodiments of the invention, complement is inhibited by upregulating expression of genes encoding such polypeptides.

Figure 2:
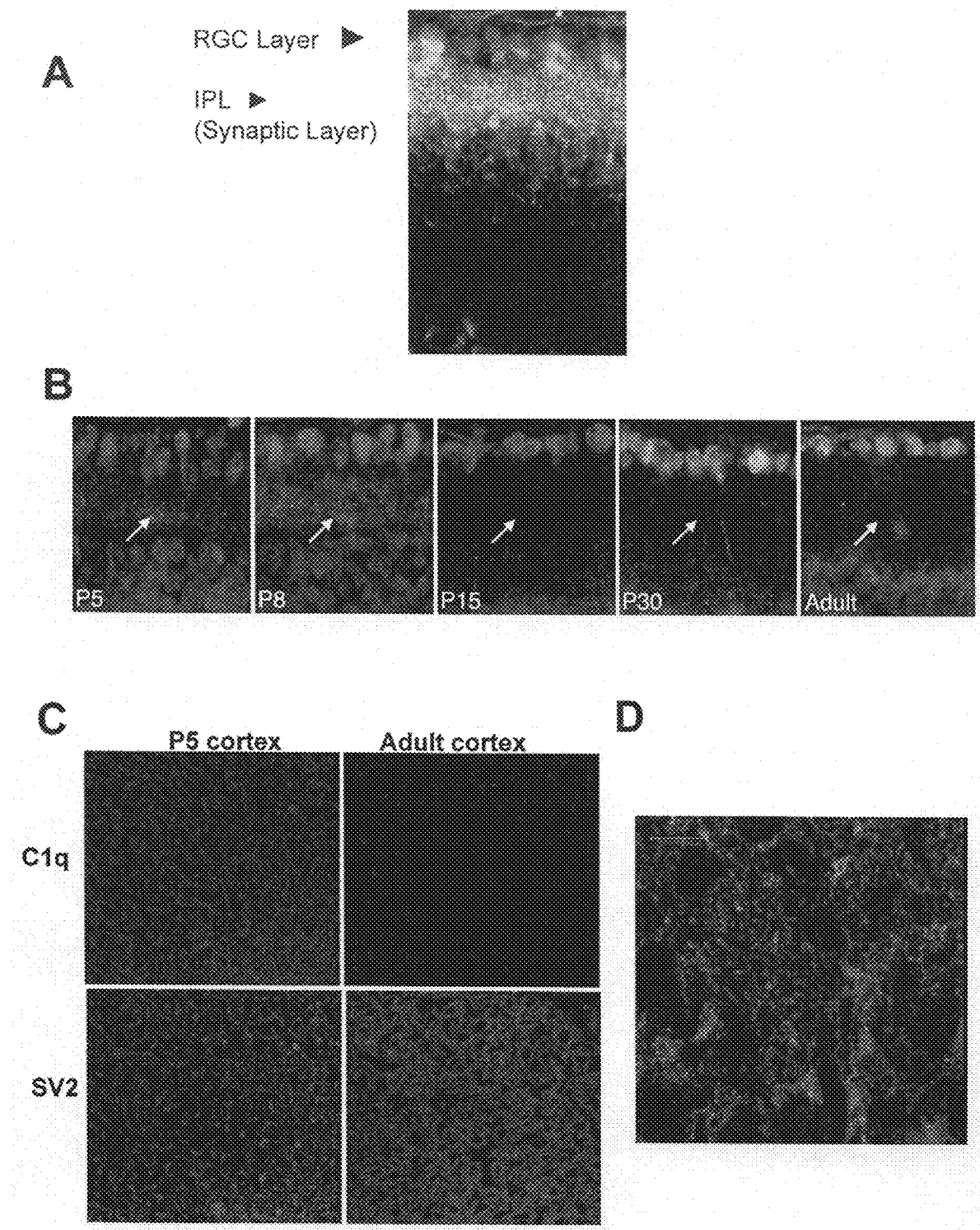
FIGS. 2A-2D. C1q is localized to developing CNS synapses in vivo. A. Longitudinal cryosection of P5 mouse retina stained with anti-C1q. A punctate pattern of C1q immunoreactivity was observed in the ganglion cell layer (GCL) and synaptic inner plexiform layer (IPL). B. Developmental localization of C1q to synapses in the IPL of the mouse retina. C Double labeling of C1q (green) with pre synaptic marker SV2 (red) demonstrate punctuate C1q-immunoreactivity in close proximity to synaptic puncta in postnatal (P5), but not adult (P45) mouse cortex. D. Higher magnification confocal image of C1q (green) and synaptic puncta in P5 mouse cortex.

Modifications of molecules that block complement activation are also known in the art. Such molecules include, without limitation, modified complement receptors, such as soluble CR1. The mature protein of the most common allotype of CR1 contains 1998 amino acid residues: an extracellular domain of 1930 residues, a transmembrane region of 25 residues, and a cytoplasmic domain of 43 residues. The entire extracellular domain is composed of 30 repeating units (FIG. 2) referred to as short consensus repeats (SCRs) or complement control protein repeats (CCPRs), each consisting of 60 to 70 amino acid residues. Recent data indicate that C1q binds specifically to human CR1. Thus, CR1 recognizes all three complement opsonins, namely C3b, C4b, and C1q. A soluble version of recombinant human CR1 (sCR1) lacking the transmembrane and cytoplasmic domains has been produced and shown to retain all the known functions of the native CR1. The cardioprotective role of sCR1 in animal models of ischemia/reperfusion injury has been confirmed. Several types of human C1q receptors (C1qR) have been described. These include the ubiquitously distributed 60- to 67-kDa receptor, referred to as cC1qR because it binds the collagen-like domain of C1q. This C1qR variant was shown to be calreticulin; a 126-kDa receptor that modulates monocyte phagocytosis. gC1qR is not a membrane-bound molecule, but rather a secreted soluble protein with affinity for the globular regions of C1q, and may act as a fluid-phase regulator of complement activation.

Decay accelerating factor (DAF) (CD55) is composed of four SCRs plus a serine/threonine-enriched domain that is capable of extensive O-linked glycosylation. DAF is attached to cell membranes by a glycosyl phosphatidyl inositol (GPI) anchor and, through its ability to bind C4b and C3b, it acts by dissociating the C3 and C5 convertases. Soluble versions of DAF (sDAF) have been shown to inhibit complement activation.

C1 inhibitor, a member of the "serpin" family of serine protease inhibitors, is a heavily glycosylated plasma protein that prevents fluid-phase C1 activation. C1 inhibitor regulates the classical pathway of complement activation by blocking the active site of C1r and C1s and dissociating them from C1q.

Peptide inhibitors of complement activation include C5a (van Oostrum et al., 1996); C5a C-terminal octapeptides (Kawai et al., 1992); C5a His67-modified C-terminal octapeptide analogues (Or et al., 1992); C089 (C5a hexapeptide, Konteatis et al., 1994); C3a C-terminus (Kretzschmar et al., 1992); Factor B-related hexapeptides (Lesavre et al., 1982); C1q B chain helical region (Fryer et al., 1997); DFP (Diisopropyl fluorophosphates, Cole et al., 1997); BCX-1470 (K-76 analog, Kaufman et al., 1995); TKIX (K-76 derivative) Sindelar et al. 1996); K-76 derivative, Tanaka 1996); FUT-175 (nafamstat mesilate, Inose rt al. 1997).

Other inhibitory molecules include Fucan (Charreau et al., 1997); Complestatin (Momota et al., 1991); Decorin (Krumdieck et al., 1992); heparin (te Velthuis et al., 1996); LU 51198 (Gralinski et al., 1997); CSPG (Kirschfink et al., 1997); L-156,602 (Tsuji et al., 1992); CVFb (Jungi and McGregor, 1979); M5 (Chen and Rael, 1997).

Conditions of Interest

By "neurological" or "cognitive" function as used herein, it is meant that the decrease of synapses in the brain enhances the patient's ability to think, function, etc. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

Among the conditions of interest for the present methods of inhibiting synapse loss are included a variety of neurodegenerative conditions, e.g. Alzheimer's disease, Down syndrome, Huntington's disease, amyotrophic lateral sclerosis, multiple sclerosis, myotonic dystrophy, glaucoma, Parkinson's disease; and the like. Such conditions benefit from administration of inhibitors of complement, including inhibitors of C1q, which allow maintenance, or reduced loss, of synapses. In some instances, where there has been neuronal loss, it may be desirable to enhance neurogenesis as well, e.g. through administration of agents or regimens that increase neurogenesis, transplantation of neuronal progenitors, etc. Agents that enhance synaptogenesis, e.g. such as thrombospondins, may also be administered.

Alzheimer's disease is a progressive, inexorable loss of cognitive function associated with an excessive number of senile plaques in the cerebral cortex and subcortical gray matter, which also contains β-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 yr; 50% die within 3 yr of onset, 20% live 5 yr, and 10% live 10 yr. Diagnostic features include onset during middle or late adult life and progressive, generalized motor involvement without sensory abnormalities. Nerve conduction velocities are normal until late in the disease.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Preventing synapse loss may maintain neuron function in these patients.

Down Syndrome is a chromosomal disorder usually resulting in mental retardation, a characteristic facies, and many other typical features, including microcephaly and short stature. In about 95% of cases, there is an extra whole chromosome 21. At autopsy, adult Down syndrome brains show the typical microscopic findings of Alzheimer's disease, and many persons also develop the associated clinical signs.

Parkinson's Disease is an idiopathic, slowly progressive, degenerative CNS disorder characterized by slow and decreased movement, muscular rigidity, resting tremor, and postural instability. In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration and Myotonic dystrophy is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (eg, diabetes mellitus). Mental retardation is common. Severely affected persons die by their early 50s.

Glaucoma is a common neurodegenerative disease that affects retinal ganglion cells (RGCs). Substantial effort is being expended to determine how RGCs die in glaucoma.

Evidence supports the existence of compartmentalised degeneration programs in synapses and dendrites, including RGCs. Recent data, from in vitro studies and from an inherited mouse model of glaucoma, suggest that molecularly distinct degenerative pathways underlie the destruction of RGC somata and RGC axons. In various neurodegenerative diseases, axons, dendrites and synapses often degenerate well before the cells die, and there is increasing evidence that this is important for the production of clinical symptoms and signs.

Huntington's disease (HD) is a hereditary progressive neurodegenerative disorder characterized by the development of emotional, behavioral, and psychiatric abnormalities; loss of previously acquired intellectual or cognitive functioning; and movement abnormalities (motor disturbances). The classic signs of HD include the development of chorea—or involuntary, rapid, irregular, jerky movements that may affect the face, arms, legs, or trunk—as well as the gradual loss of thought processing and acquired intellectual abilities (dementia). There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Multiple Sclerosis is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

The methods of the invention can find use in combination with cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive; non-tumorigenic interspersion with host progenitors and their progeny. Human NSCs are capable of expressing foreign transgenes in vivo in these disseminated locations. A such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. By synapse loss enhancers, the functional connections of the neurons are enhances, providing for an improved clinical outcome.

METHODS OF TREATMENT

The methods of the invention provide for modulating synapse loss through administering agents that are agonists or antagonists of complement. Without being bound by theory, the data provided herein demonstrate that immature astrocytes induce expression of C1q proteins in neurons during development. During the developmental process of synapse elimination, this C1q expression can be coupled with a signal for complement activation, e.g. β-amyloid, APP, cytokines such as IFNγ, TNFα, and the like, thereby eliminating specific synapses. This development pathway may be inappropriately activated in neurodegenerative disease, resulting in the undesirable loss of synapses. By administering agents that alter complement activation, synapses can be maintained that would otherwise be lost. Such agents include C1q inhibitors, agents that upregulate expression of native complement inhibitors, agents that down-regulate C1q synthesis in neurons, agents that block complement activation, agents that block the signal for complement activation, and the like.

The methods promote improved maintenance of neuronal function in conditions associated with synapse loss. The maintenance of neural connections provides for functional improvement in neurodegenerative disease relative to untreated patients. The prevention of synapse loss may comprise at least a measurable improvement relative to a control lacking such treatment, for example at least a 10% improvement in the number of synapses, at least a 20% improvement, at least a 50% improvement, or more.

The agents of the present invention are administered at a dosage that decreases synapse loss while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials.

Therapeutic agents, e.g. inhibitors of complement, activators of gene expression, etc. can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration may be carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing LD50 animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. some agents may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy-aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Gene Delivery

One approach for modulating synapse loss involves gene therapy. In such methods, anti-sense or RNAi sequences encoding C1q or fragments thereof are introduced into the neurons, and expressed as a means of decreasing C1q expression in the targeted synapses. To genetically modify neurons that are protected by the BBB, two general categories of approaches have been used. In one type of approach, cells are genetically altered, outside the body, and then transplanted somewhere in the CNS, usually in an area inside the BBB. In the other type of approach, genetic "vectors" are injected directly into one or more regions in the CNS, to genetically alter cells that are normally protected by the BBB. It should be noted that the terms "transfect" and "transform" are used interchangeably herein. Both terms refer to a process which introduces a foreign gene (also called an "exogenous" gene) into one or more preexisting cells, in a manner which causes the foreign gene(s) to be expressed to form corresponding polypeptides.

A preferred approach introduces into the CNS a source of a desirable sequence, by genetically engineering cells within the CNS. This has been achieved by directly injecting a genetic vector into the CNS, to introduce foreign genes into CNS neurons "in situ" (i.e., neurons which remain in their normal position, inside a patient's brain or spinal cord, throughout the entire genetic transfection or transformation procedure).

Useful vectors include viral vectors, which make use of the lipid envelope or surface shell (also known as the capsid) of a virus. These vectors emulate and use a virus's natural ability to (i) bind to one or more particular surface proteins on certain types of cells, and then (ii) inject the virus's DNA or RNA into the cell. In this manner, viral vectors can deliver and transport a genetically engineered strand of DNA or RNA through the outer membranes of target cells, and into the cells cytoplasm. Gene transfers into CNS neurons have been reported using such vectors derived from herpes simplex viruses (e.g., European Patent 453242, Breakfield et al 1996), adenoviruses (La Salle et al 1993), and adeno-associated viruses (Kaplitt et al 1997).

Non-viral vectors typically contain the transcriptional regulatory elements necessary for expression of the desired gene, and may include an origin of replication, selectable markers and the like, as known in the art. The non-viral genetic vector is then created by adding, to a gene expression construct, selected agents that can aid entry of the gene construct into target cells. Several commonly-used agents include cationic lipids, positively charged molecules such as polylysine or polyethylenimine, and/or ligands that bind to receptors expressed on the surface of the target cell. For the purpose of this discussion, the DNA-adenovirus conjugates described by Curiel (1997) are regarded as non-viral vectors, because the adenovirus capsid protein is added to the gene expression construct to aid the efficient entry of the gene expression construct into the target cell.

In cationic gene vectors, DNA strands are negatively charged, and cell surfaces are also negatively charged. Therefore, a positively-charged agent can help draw them together, and facilitate the entry of the DNA into a target cell. Examples of positively-charged transfection agents include polylysine, polyethylenimine (PEI), and various cationic lipids. The basic procedures for preparing genetic vectors using cationic agents are similar. A solution of the cationic agent (polylysine, PEI, or a cationic lipid preparation) is added to an aqueous solution containing DNA (negatively charged) in an appropriate ratio. The positive and negatively charged components will attract each other, associate, condense, and form molecular complexes. If prepared in the appropriate ratio, the resulting complexes will have some positive charge, which will aid attachment and entry into the negatively charged surface of the target cell. The use of liposomes to deliver foreign genes into sensory neurons is described in various articles such as Sahenk et al 1993. The use of PEI, polylysine, and other cationic agents is described in articles such as Li et al 2000 and Nabel et al 1997.

An alternative strategy for introducing DNA into target cells is to associate the DNA with a molecule that normally enters the cell. This approach was demonstrated in liver cells in U.S. Pat. No. 5,166,320 (Wu et al 1992). An advantage of this approach is that DNA delivery can be targeted to a particular type of cell, by associating the DNA with a molecule that is selectively taken up by that type of target cell. A limited number of molecules are known to undergo receptor mediated endocytosis in neurons. Known agents that bind to neuronal receptors and trigger endocytosis, causing them to enter the neurons, include (i) the non-toxic fragment C of tetanus toxin (e.g., Knight et al 1999); (ii) various lectins derived from plants, such as barley lectin (Horowitz et al 1999) and wheat germ agglutinin lectin (Yoshihara et al 1999); and, (iii) certain neurotrophic factors (e.g., Barde et al 1991). At least some of these endocytotic agents undergo "retrograde" axonal transport within neuron. The term "retrograde", in this context, means that these molecules are actively transported, by cellular processes, from the extremities (or "terminals") of a neuron, along an axon or dendrite, toward and into the main body of the cell, where the nucleus is located. This direction of movement is called "retrograde", because it runs in the opposite direction of the normal outward ("anterograde") movement of most metabolites inside the cell (including proteins synthesized in the cell body, neurotransmitters synthesized by those proteins, etc.).

COMPOUND SCREENING

In one aspect of the invention, candidate agents are screened for the ability to modulate synapse loss, which agents may include candidate complement inhibitors, variants, fragments, mimetics, agonists and antagonists. Such compound screening may be performed using an in vitro model, a genetically altered cell or animal, or purified protein. A wide variety of assays may be used for this purpose. In one embodiment, compounds that are predicted to be antagonists or agonists of complement, including specific complement proteins, e.g. C1q, and complement activating signals, e.g. β-amyloid, APP, etc. are tested in an in vitro culture system, as described below.

For example, candidate agents may be identified by known pharmacology, by structure analysis, by rational drug design using computer based modeling, by binding assays, and the like. Various in vitro models may be used to determine whether a compound binds to, or otherwise affects complement activity. Such candidate compounds are used to contact neurons in an environment permissive for synapse loss. Such compounds may be further tested in an in vivo model for an effect on synapse loss.

Screening may also be performed for molecules produced by astrocytes, e.g. immature astrocytes, which induce C1q expression in neurons. In such assays, co-cultures of neurons and astrocytes are assessed for the production or expression of molecules that induce C1q expression. For example, blocking antibodies may be added to the culture to determine the effect on induction of C1q expression in neurons.

Synapse loss is quantitated by administering the candidate agent to neurons in culture, and determining the presence of synapses in the absence or presence of the agent. In one embodiment of the invention, the neurons are a primary culture, e.g. of RGCs. Purified populations of RGCs are obtained by conventional methods, such as sequential immunopanning. The cells are cultured in suitable medium, which will usually comprise appropriate growth factors, e.g. CNTF; BDNF; etc. The neural cells, e.g. RCGs, are cultured for a period of time sufficient allow robust process outgrowth and then cultured with a candidate agent for a period of about 1 day to 1 week. In many embodiments, the neurons are cultured on a live astrocyte cell feeder in order to induce signaling for synapse loss. Methods of culturing astrocyte feeder layers are known in the art. For example, cortical glia can be plated in a medium that does not allow neurons to survive, with removal of non-adherent cells.

For synapse quantification, cultures are fixed, blocked and washed, then stained with antibodies specific synaptic proteins, e.g. synaptotagmin, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved to disk for analysis.

The term "agent" as used herein describes any molecule, e.g. protein or pharmaceutical, with the capability of modulating synapse loss, particularly through the complement pathway. Candidate agents also include genetic elements, e.g. anti-sense and RNAi molecules to inhibit C1q expression, and constructs encoding complement inhibitors, e.g. CD59, and the like. Candidate agents encompass numerous chemical classes, though typically they are organic molecules, including small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., Pac. Symp. Biocompat. 305-16, 1998); Sun et al., J. Comput. Aided Mol. Des. 12:597-604, 1998); each incorporated herein by reference in their entirety). For example, libraries of phosphatase inhibitors can be prepared by syntheses of combinatorial chemical libraries (see generally DeWitt et al., Proc. Nat. Acad. Sci. USA 90:6909-13, 1993; International Patent Publication WO 94/08051; Baum, Chem. & Eng. News, 72:20-25, 1994; Burbaum et al., Proc. Nat. Acad. Sci. USA 92:6027-31, 1995; Baldwin et al., J. Am. Chem. Soc. 117:5588-89, 1995; Nestler et al., J. Org. Chem. 59:4723-24, 1994; Borehardt et al., J. Am. Chem. Soc. 116:373-74, 1994; Ohlmeyer et al., Proc. Nat. Acad. Sci. USA 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on synapse loss. The animal models utilized in validation studies generally are mammals. Specific examples of suitable animals include, but are not limited to, primates, mice, and rats.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Methods

RGC Gene Expression Analysis Using Affymetrix GeneChip Arrays: Purified RGCs were plated at a density of ~100,000 cells per well in 6-well dishes and cultured in the presence or absence of a live astrocyte feeding layer for four days. Total RNA was harvested using RNeasy Mini Kit (Qiagen). cDNA was synthesized from 2 µg total RNA using the Gibco BRL Superscript Choice system and a T7-(dT)24 primer [5'-GGCCAG-TGAATTGTAATACGACTCACTATAGG-GAGGCGG-(dT)24-3'] (SEQ ID NO:1). Biotinylated cRNA target was prepared by T7 linear amplification using the Bioarray RNA Transcripts Labeling Kit (Enzo) followed by fragmentation. Target was hybridized to Affymetrix Test-2 GeneChip arrays to assess target performance and the Rat U34 genome GeneChip array set following standard Affymetrix protocols. Microarray data was generated in paired triplicates from three independent cultured RGC preparations. Assessment of the quality of sample data and changes in gene expression were analyzed with MicroArray Suite 5.0 software. Genes identified as changing in expression in response to astrocytes increased or decreased at least 2-fold in all three replicates.

Semiquantitative RT-PCR: Total RNA was prepared as above from RGCs cultured alone or with an astrocyte feeding layer, astrocyte conditioned medium or 5 µg/ml TSP1 for six days. 1 µg total RNA was reverse-transcribed using RETROScript (Ambion) and 1/20th of resulting cDNA product was used for PCR. The following PCR primers were used: F-rC1q B (5'-cggaattcccttctctgccctgaggacgg-3') (SEQ ID NO:2), R-rC1q B (5'-cgggat-cctttctgcatgcggtctcggtc-3') SEQ ID NO:3), F-mC1qA (5'-cggaattcgacaaggtcc-tcaccaaccag-3') (SEQ ID NO:4), R-mC1qA (5'-cgggatccggggtccttctcgatcc-3') (SEQ ID NO:5), F-mC1qC (6-ccggggggagccaggtgtggag-3') (SEQ ID NO:6), R-mC1qC (5'-gcacaggttggc-cgtatgcg-3') (SEQ ID NO:7). GAPDH primers were added to all reactions as an internal control (gapdh-s: 5'-GGTCTTACTCCTTG-GAGGCCATGT-3' SEQ ID NO:8); gapdh-as: 5'-GAC-CCCTTCA-T-TGACCTCAACTACA-3' (SEQ ID NO:9)). 2×PCR Mater Mix kit (Promega) was used as supplied by manufacturer with the exception of the addition of 4 mM MgCl2 (5.5 mM final) to the C1qC reaction mix. PCR program was as follows: initial denaturation for 4 min at 94° C.; cycle denaturation for 1 min at 94° C., annealing for 30 s at 55° C., and extension for 30 sec at 72° C. (30 cycles total); final extension for 10 min at 72° C. The PCR products were fractionated on 1.5% agarose gel and visualized by ethidium bromide staining. Results shown are representative of three biological replicates.

Preparation of astrocytes. Cortical glia were prepared as described (Ullian et al., 2001). Briefly, P1-P2 cortices were papain-digested and plated in tissue culture flasks (Falcon) in a medium that does not allow neurons to survive (Dulbecco's Modified Eagle Medium, fetal bovine serum (10%), penicillin (100 U/ml), streptomycin (100 µg/ml), glutamine (2 mM) and Na-pyruvate (1 mM). After 4 days non-adherent cells were shaken off of the monolayer and cells were incubated another 2-4 days to allow monolayer to refill.

Medium was replaced with fresh medium containing AraC (10 µM) and incubated for 48 hours. Astrocytes were trypsinized and plated onto 24-well inserts (Falcon, 1.0 µm) or 10 cm tissue culture dishes.

Purification and culture of RGCs. RGCs were purified by sequential immunopanning to greater than 99.5% purity from P5 mice or Sprague-Dawley rats (Simonsen Labs, Gilroy, Calif.), as previously described (Barres et al., 1988). Approximately 30,000 RGCs were cultured per well in 24-well plates (Falcon) on glass (Assistant) or Aclar 22C (Allied Signal) coverslips coated with poly-D-lysine (10 µg/ml) followed by laminin (2 µg/ml). RGCs were cultured in 600 µl of serum-free medium, modified from Bottenstein and Sato (1979), containing Neurobasal (Gibco), bovine serum albumin, selenium, putrescine, triiodothyronine, transferrin, progesterone, pyruvate (1 mM), glutamine (2 mM), CNTF (10 ng/ml), BDNF (50 ng/ml), insulin (5 µg/ml), and forskolin (10 µM). Recombinant human BDNF and CNTF were generously provided by Regeneron Pharmaceuticals. TTX and Picrotoxin from RBI. All other reagents were obtained from Sigma.

Labeling of Retinogeniculate Afferents. Mouse pups were anesthetized with inhalant isofluorane. Mice received intravitreal injections of Cholera Toxin-subunit (CT□) conjugated to Alexa 488 (green label) in the left eye, and CT□ conjugated to Alexa 594 (red label) into the right eye (2-3 µl; 0.5% in sterile saline; Molecular Probes, Eugene OR; Conn.). 24 hours later mice were transcardially perfused with 4% paraformaldyhyde (ages in text correspond to age at sacrifice), brain tissue was postfixed overnight, cryoprotected in 30% sucrose and then sectioned coronally at 40 µm, mounted onto gelatin-coated slides and coverslipped with Vectashield (Vector Laboratories; Burlingame, Calif.).

Image quantification and preparation of photomicrographs. Images were digitally acquired with a 3900×3600 pixel color CCD camera (Axiocam; Zeiss; Thornwood, N.Y.). Universal gains and exposures were established for each label. Raw images of the dLGN were imported to Photoshop (Adobe) and cropped to exclude the vLGN and IGL, then the degree of left and right eye axon overlap was quantified using the multi-threshold protocol described in Torborg et al. (2005). This technique is designed to compare overlap across a range of signal:noise values in WT versus transgenic mice. This approach best allows for direct statistical comparison of overlap between various strains of mice at different ages and has been used by others as well (Pak et al., 2004). After quantification, images were imported to Photoshop (Adobe) for adjustments to intensity, cropping, and alignment. In some cases, artifact was removed from outside the boundaries of the dLGN.

The Classical Complement Cascade Mediates Developmental CNS Synapse Elimination During development, activity-dependent competition between axons for synaptic territory causes permanent removal of synaptic connections, but what determines which synapses will be eliminated? Excess numbers of synapses are first generated to establish the initial wiring pattern of the brain, but the formation of mature, precise neural circuits requires the selective elimination and pruning of inappropriate synaptic connections.

Much of our understanding of developmental synapse elimination in the brain come from studies carried out in the developing visual system. The retinogeniculate system has proven an excellent model system for studying CNS developmental synapse elimination in vivo. In all binocular animals, axons from retinal ganglion cells (RGCs) terminate in distinct non-overlapping eye-specific domains in the dorsal lateral geniculate nucleus (dLGN). This segregation of retinogeniculate projections into eye-specific territories occurs over a specific and well characterized period in postnatal development, and reflects the elimination of thousands of synapses within incorrect LGN territory and the expansion of axon terminals and formation of synapses within the correct eye specific regions. Synapse elimination also occurs within monocular regions of the LGN during a two week period spanning eye opening (P8-P30 in mouse). Initially, neurons in the rodent dLGN are innervated by multiple (>10) RGC axons, but by the third week of postnatal development, each dLGN neurons receive stable inputs from 1-2 RGC axons. Much like the neuromuscular junction in the peripheral nervous system, this developmental shift in synaptic convergence represents the permanent elimination of inappropriate retinogeniculate synapses, and the maintenance and strengthening of appropriate synaptic connections.

The appearance of astrocytes at synapses in the postnatal brain coincides with this dynamic period of synapse formation and elimination. It has been estimated that fine processes of astrocytes can ensheath as many as 40,000 synapses, and recent research indicate a pivotal role for astrocyte-derived signals in the development of structural and functional of synapses in the brain. Thrombospondin was recently identified as a critical astrocyte-secreted synaptogenic signal, and astrocytes likely secrete other signals that control the development and stabilization of functional synapses.

Here we identify an unexpected and novel role for astrocytes and the classical complement cascade in CNS synapse elimination. The complement system is part of the innate immune system, and is our first line of defense against pathogens and infection. Gene chip studies revealed that only one gene was profoundly up-regulated in neurons by astrocytes; complement protein C1q. C1q's best known role in the immune system is to promote elimination of dead cells, pathogens, and debris. The classical cascade is a triggered enzyme cascade activated by the binding (opsonization) of C1q directly to the membrane surface. C1q opsonization can eliminate unwanted cells by "tagging" them for removal by resident phagocytes, or by further activating the downstream proteases, which ultimately leads to the cleavage of the major complement protein, C3. Like C1q, activated C3 fragments (C3b, C3ib) can directly opsonize cells for phagocytosis, or eliminate unwanted cells via terminal activation of the cascade and the formation of the lytic membrane attack complex.

We hypothesized that complement opsonizes or "tags" synapses for selective elimination during development. The findings reported herein identify C1q and the classical complement cascade as a novel and important mediator of synapse elimination in the developing visual system. In the adult CNS, synapse loss often occurs long before clinical symptoms in many neurodegenerative diseases. We also provide evidence that this complement-dependent mechanism of synapse elimination may be recapitulated in early stages of neurodegenerative diseases, such as glaucoma.

Results

Astrocytes up-regulate C1q in CNS neurons. We used a genomic approach to screen candidate neuronal genes that are regulated by astrocytes. We took advantage of our ability to grow purified retinal ganglion cells (RGCs) in the complete absence of glia or other retinal cell types. RGCs cultured for several days below a feeding layer of astrocytes have 7-fold more functional synapses than RGCs cultured alone. We used this established experimental paradigm to investigate astrocyte-dependent neuronal gene expression. RNA was collected from postnatal RGCs that had been grown for one week in the presence or absence of astrocytes, and target RNA was hybridized to an Affymetrix gene chip as previously described.

Surprisingly, only one neuronal gene was significantly up-regulated by astrocytes. This gene was identified as complement C1q, an immune system protein thought not to be normally expressed in the brain. C1q is a large multimeric secreted protein composed of six identical subunits with globular heads and long collagen-like tails (Kishore and Reid, 2000). C1q consists of 18 polypeptide chains (6 C1qA chains, 6 C1q B chains, and 6 C1q C chains). We found that all 3 subunits of C1q were up-regulated in purified RGCs by 10-30-fold upon exposure to astrocyte feeding layer (FIG. 1A). The astrocyte-induced increase in C1q A, B, and C mRNA levels in RGC neurons was verified using semi-quantitative RT-PCR (FIG. 1B). Consistent with our in vitro experiments, C1q is highly expressed in retinal ganglion cells in vivo. RT-PCR analysis of mRNA isolated from RGCs that were acutely isolated (P5) indicate expression of C1q (FIG. 1C). In addition, C1q mRNA was detected in samples of perfused postnatal mouse retina. C1q levels were highest in the early postnatal retina (P5-P10), and declined precipitously after P15 (FIG. 1C). This developmental expression pattern for astrocyte-induced C1q gene expression in neurons corresponds to the appearance of astrocytes in the postnatal CNS, and the period of synaptic refinement of retinal axons in the visual system, and suggests the possibility that C1q has a functional role in synaptic pruning.

Figure 9:
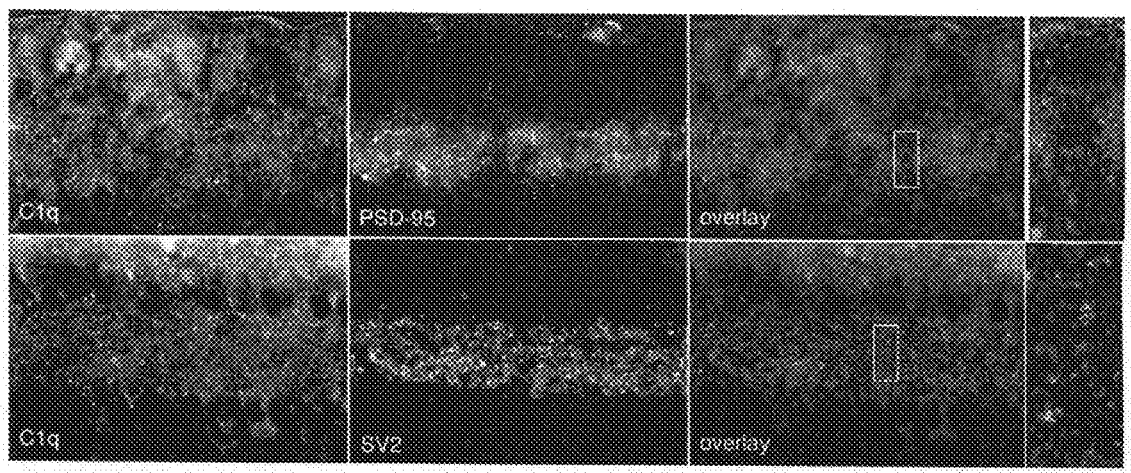
FIGS. 9A-9B. A. C1q-positive puncta in the IPL of postnatal mice were in close apposition with synaptic puncta identified by co-immunostaining with pre and post-synaptic markers, PSD95 (top) and SV2 (bottom). B. The synaptic pattern of C1q immunoreactivity in the retina (left) was not detected after preadsorbing C1q antibodies with purified C1q protein (right).
Figure 9:
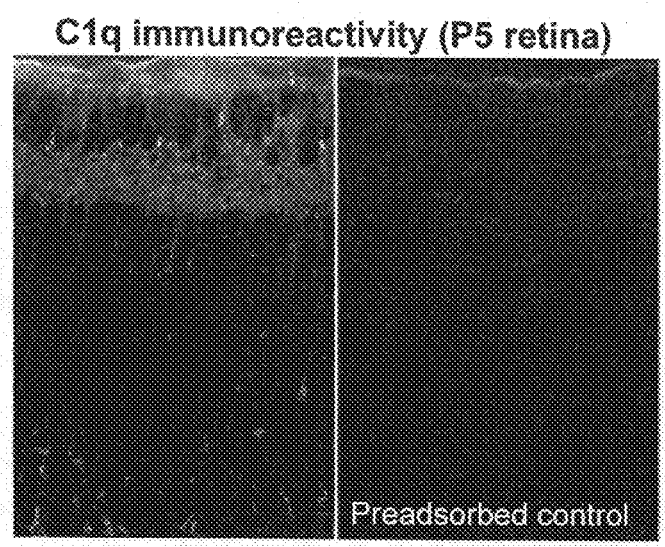

C1q is expressed at synapses in the developing CNS. We performed immunostaining experiments in cryosections of rodent tissue at different developmental timepoints. Using several different C1q antisera, we found a bright, punctate pattern C1q immunoreactivity throughout the developing brain and retina. Punctate C1q immunoreactivity was highly localized to the synaptic inner plexiform layer (IPL) of postnatal mouse retinas, and was also observed in a subset of developing RGCs (FIG. 2A). Consistent with the expression pattern of C1q mRNA in the postnatal retina (FIG. 1C), we found that C1q protein expression and synaptic localization follow a similar developmental pattern (FIG. 2B). In addition, many C1q-positive puncta in the IPL were in close apposition with synaptic puncta identified by co-immunostaining with pre and post-synaptic markers (FIG. 9A).

C1q protein is also highly expressed in synaptic regions of early postnatal rodent brain (P4-P10) (FIG. 2C). Double labeling with synaptic antibodies such as SV2, demonstrate punctate C1q-immunoreactivity in close proximity to synaptic puncta (FIG. 2D). As in the retina, the synaptic pattern of C1q immunoreactivity in the brain was not observed in adult rodent brain sections, suggesting that C1q is localized to synapses in developing, but not adult brain. This synaptic pattern of C1q immunoreactivity was not detected when the same antibodies were used to stain brain sections prepared from C1q A-deficient mice, or after preadsorbing C1q antibodies with purified C1q protein (FIG. 9B).

C1q is required for normal retinogeniculate refinement. To determine whether C1q play a functional role in developmental synapse elimination in vivo, we focused on the development of the retino-geniculate synapse. Using a combination of neuroanatomical and electrophysiological techniques, we investigated synaptic refinement and synapse elimination in the dLGN of mice that lack the A chain of C1q (C1q KO). These mice have no gross neuroanatomical or behavioral defects, despite their inability to express functional C1q protein, or to activate the classical complement cascade.

To visualize the pattern of retinogeniculate projections, we performed anterograde tracing of RGC afferents by injecting the β subunit of cholera toxin conjugated to Alexa 594 (CTβ-594) dye (red) and CTβ-Alexa 488 (green) into respective left and right eyes of wild type and C1q KO mice at several postnatal ages (P5, P10 and P30). In the mouse LGN, eye-specific territories are established between P4-P8, such that by P10, axons from the ipsilateral eye have segregated into a small eye-specific patch in the medial dLGN. LGN inputs are further refined over the next two postnatal weeks, such that by P30, left and right eyes are completely segregated in to tight eye-specific territories, with minimal intermingling between RGC axons originating from left and right eyes.

Figure 3:
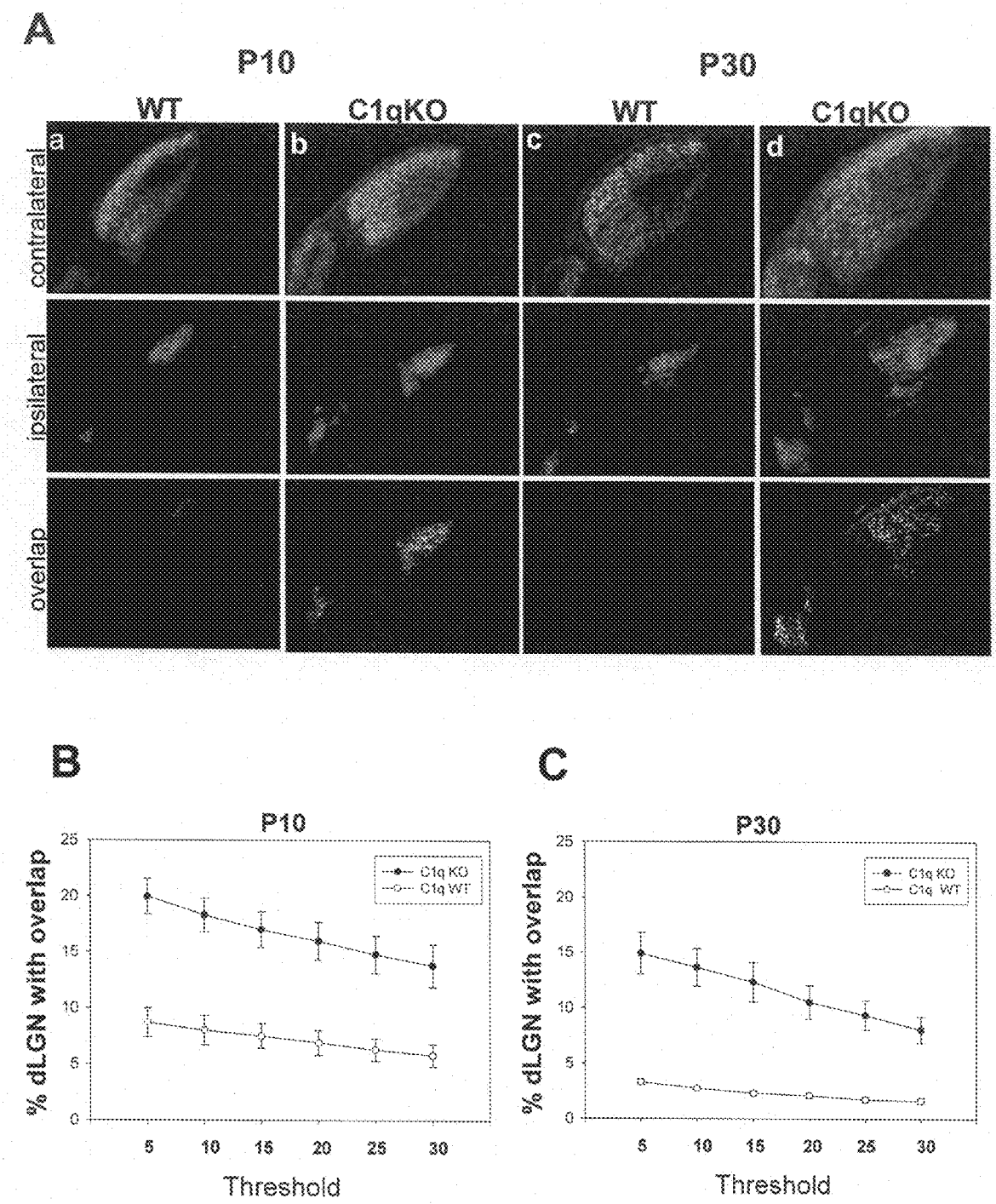
FIGS. 3A-3C. C1q-deficient mice have defects in synaptic refinement and eye-specific segregation. A. C1q KO mice at P10 (left two rows) and P30 (last two rows) have expanded ipsilateral projections (red) and significant intermingling (overlap) between RGC axons from left and right eyes (yellow) compared to littermate WT controls. Retinogeniculate projection patterns were visualized after injecting βcholera toxin conjugated to Alexa 594 (CTb-594) dye (red) and CTb488 (green) into left and right eyes of WT and C1q KO mice. Quantification of the percentage of dLGN receiving overlapping inputs from the ipsilateral eye in C1q KO vs WT controls at P10 (B) and P30 (C). C1q KO mice exhibit significantly more overlap than WT mice, regardless of threshold.

We found that C1qA KO mice have significant defects in LGN refinement and segregation. At P10, the amount of dLGN territory occupied by contralateral retinal projections was notably larger, and in many cases, the ipsilateral projections appeared more diffuse in C1q KOs compared to wild type mice and litter mate controls (FIG. 3A, column a vs b). Consistent with these observations, the dLGN in C1q KO mice have significant defects in eye-specific segregation. We observed significant overlap between left and right eye RGC projections in the dLGN of C1q KOs (FIG. 3A, column a vs b, bottom row). These data were quantified using a well-established threshold-independent method of analysis, and indicate that C1q KOs had a significantly higher percentage of overlapping projections at all thresholds examined (Insert updated stats n=) (FIG. 3B).

Figure 10:
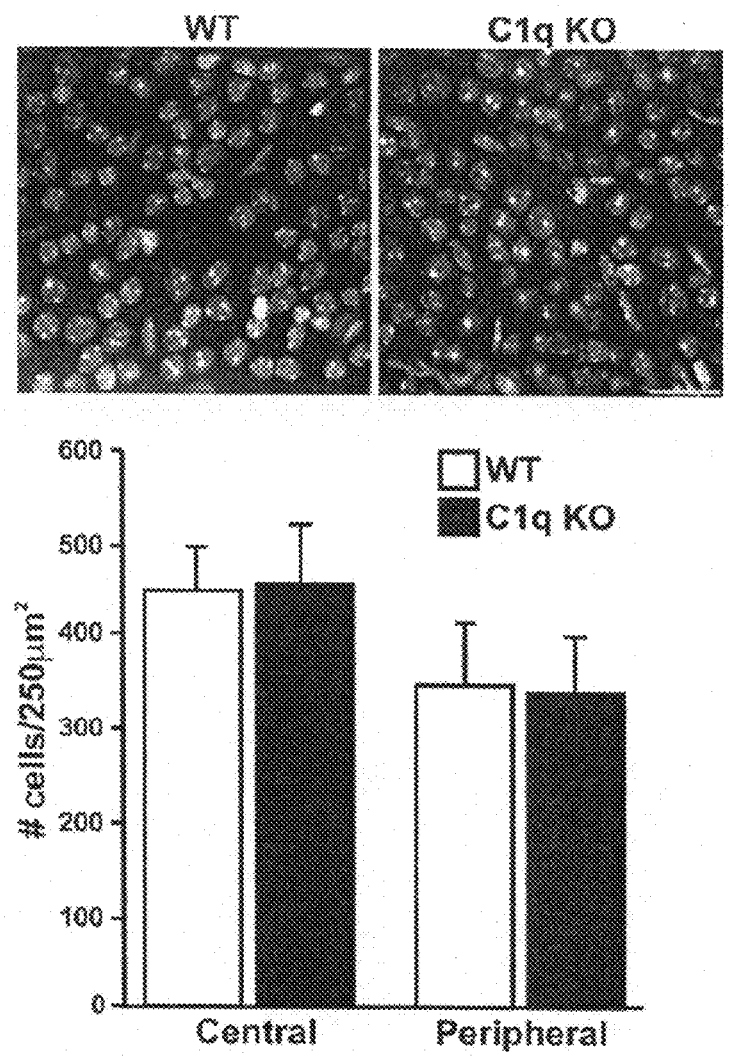
FIG. 10. Whole mount retinas stained with nuclear dye, DAPI shown that there were no significant differences in the number of cells in the peripheral or central regions of whole mount retinas in C1q KO and controls.

Surprisingly, significant segregation defects were still evident in juvenile C1q KO mice (FIG. 3B, column c vs d, bottom row). Normally, by P30, there is very little overlap between the two eyes (<3% of dLGN have overlapping projections), but as shown in FIG. 10, C1q KO mice had significant overlapping retinal projections, and these effects were threshold-independent. The phenotype at P30 was similar to that observed at P10, suggesting that many LGN neurons remain binocularly innervated long after the bulk of eye-specific segregation has occurred in the mouse (by P10). The pattern of RGC inputs to the dLGN appeared normal in C1q KO mice at P4-P5, a time point before significant segregation occurs, which suggests that refinement defects in C1q KO mice are not likely due to axonal pathfinding defects. In addition, these segregation defects can not be explained by differences in the number of RGCs in C1q KO mice. There were no significant differences in the number of cells in the peripheral or central regions of whole mount retinas in C1q KO and controls (FIG. 10).

Figure 11:
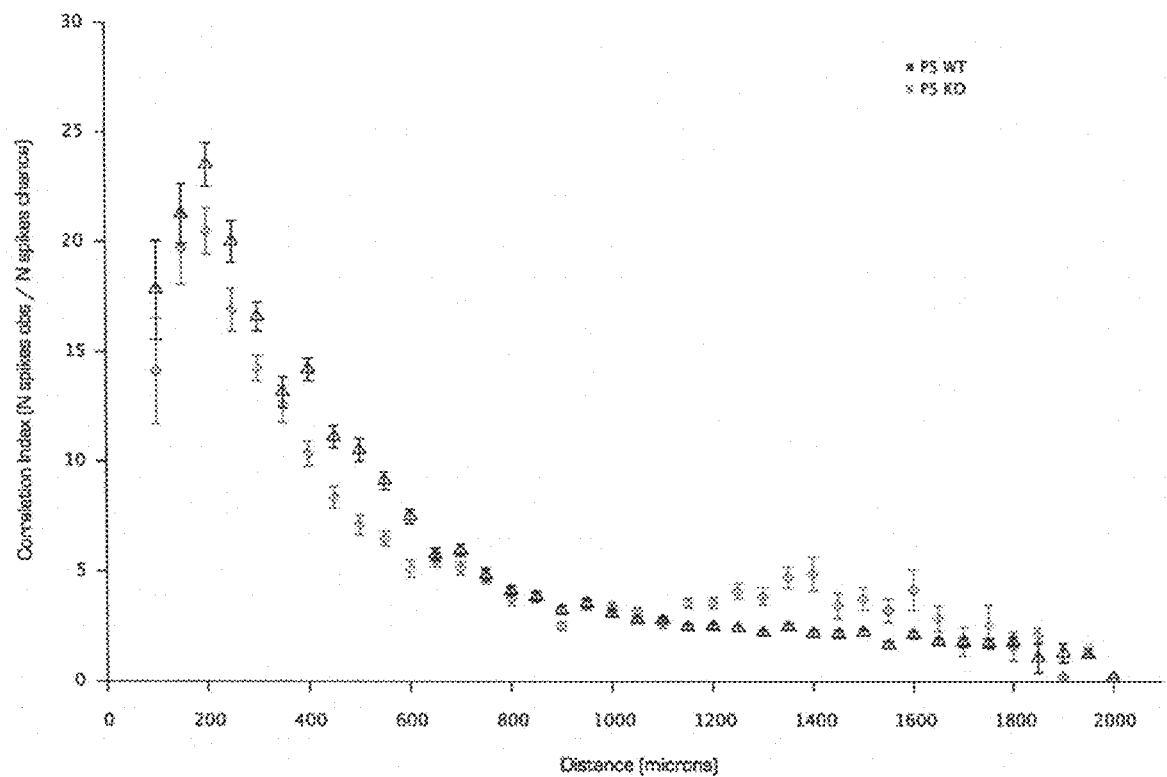
FIG. 11. Multielectrode recordings of RGC firing patterns indicate that C1q-deficient mice have normal retinal waves. In both WT and C1qKO retinas (P5), neighboring ganglion cells are more correlated in their firing than those located at further distances from one another.
Figure 12:
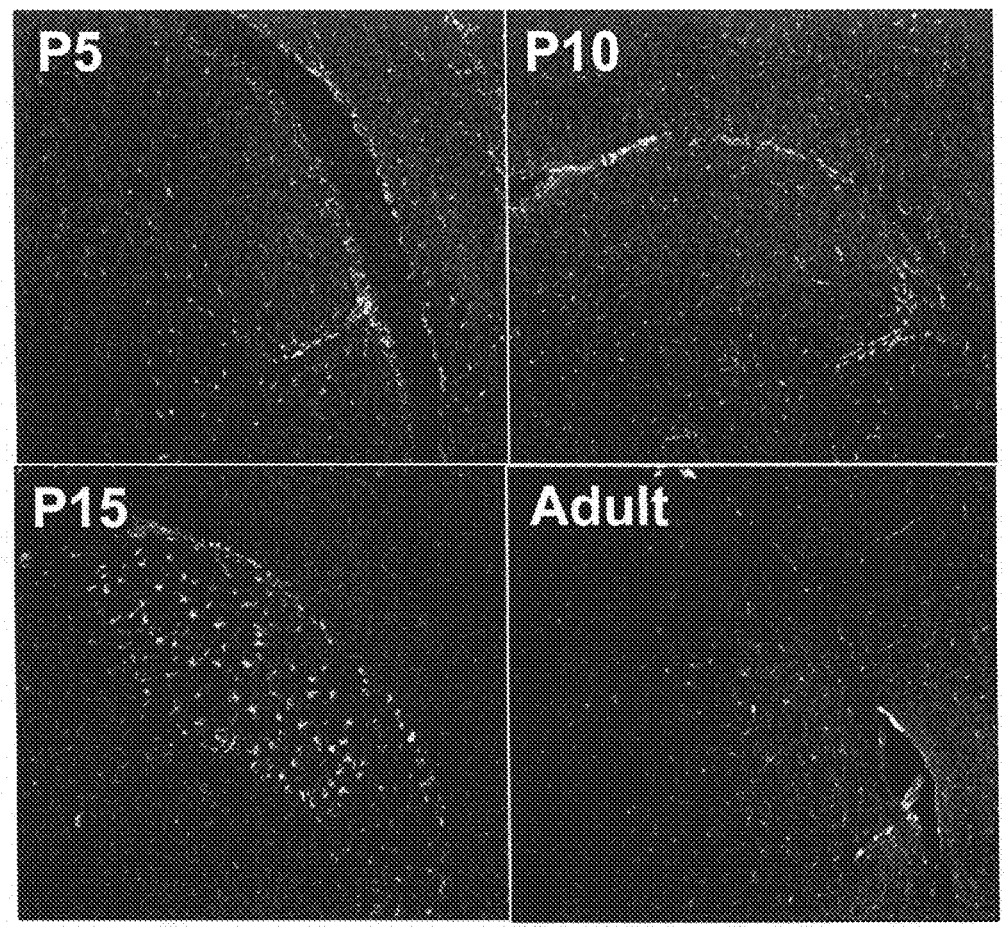
FIGS. 12A-12B. Microglia, the resident phagocytes in the brain, express receptors for complement (C3 and C1q). Phagocytic microglia in dLGN were stained with anti-CD68 at different developmental timepoints. CD68+ microglia most strongly label the dLGN at P15, a time of active synapse elimination. B. An example of engulfment of RGC terminals (red, CTβ) by CD68+ microglia (green) were observed in the dLGN during the synapse elimination period (P10-P15).
Figure 12:
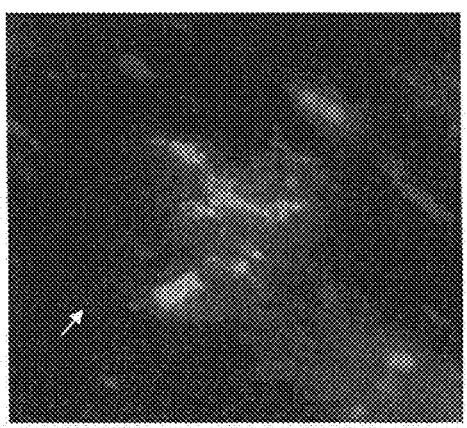
Figure 13:
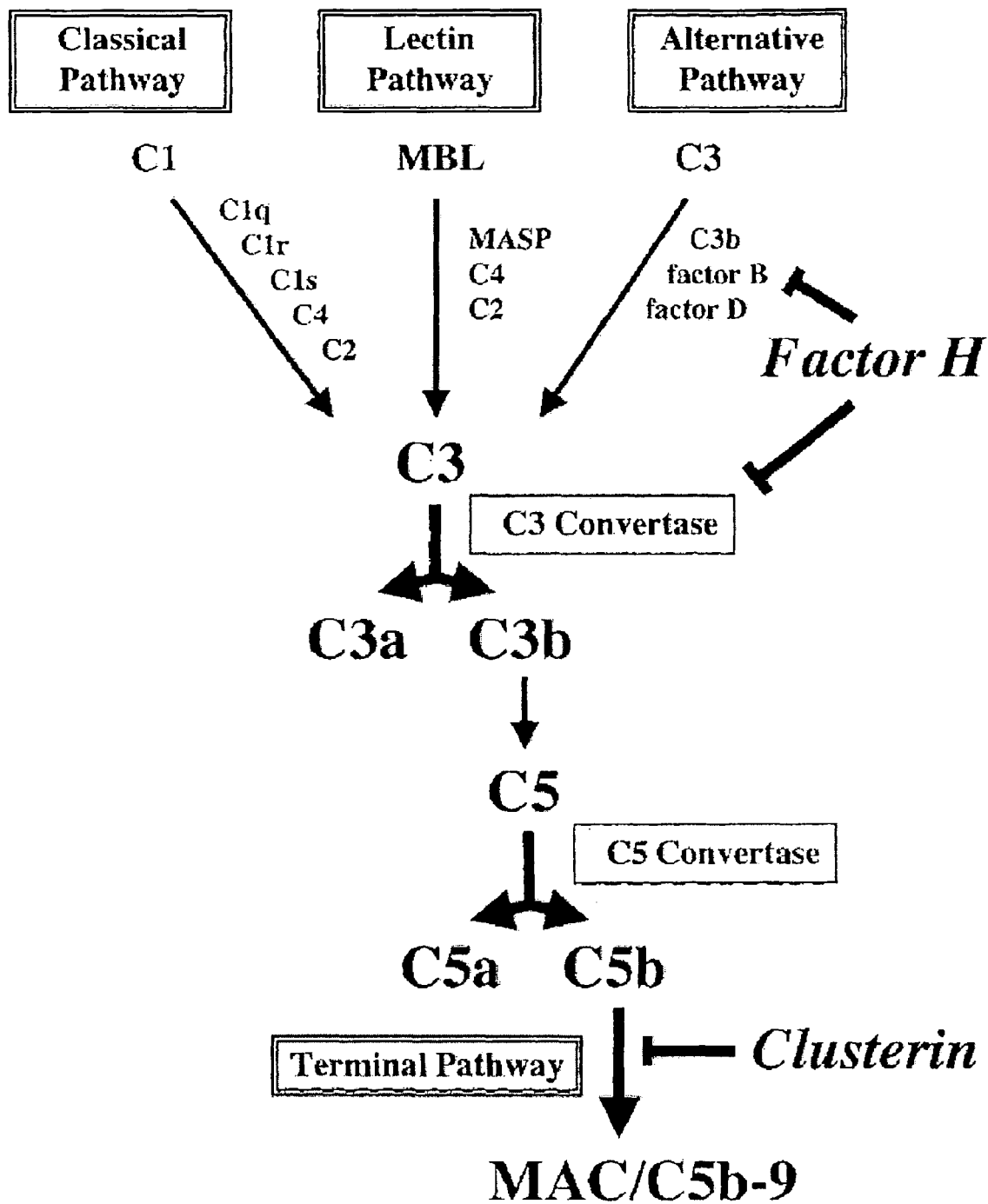
FIG. 13. Complement pathway.

Spontaneous retinal activity has been shown to drive eye specific segregation in several species, including mouse. Retinal waves are composed of bursts of action potentials that correlate the firing of neighboring RGCs, while the firing of more distant RGC is less correlated. In order to be sure that the segregation defects we measured in C1q KOs were not secondary to effects of abnormal retinal activity in C1qKO mice, we measured retinal waves in retinas dissected from P5 C1qKOs and age matched wild type controls. Multielectrode recordings of RGC firing patterns clearly indicate that C1q-deficient mice have normal retinal waves. In both WT and C1qKO retinas, neighboring ganglion cells are more correlated in their firing than those located at further distances from one another (FIG. 11).

LGN neurons remain multiply innervated in C1q KO mice. The segregation of retinal axons into eye-specific territories is a well-established assay for studying developmental synapse refinement, but synapse elimination also occurs in the monocular regions of the dLGN. Electrophysiological recordings of neurons in the contralateral LGN indicate that even after the bulk of RGC axons have segregated in to eye specific territories, synapse elimination continues to occur during the 2 weeks after eye opening. Initially (P4-P10), dLGN neurons are innervated by multiple (ie>10) RGC axons, but by the fourth week of postnatal development, each dLGN neurons receive stable inputs from 1-2 RGC axons.

Figure 4:
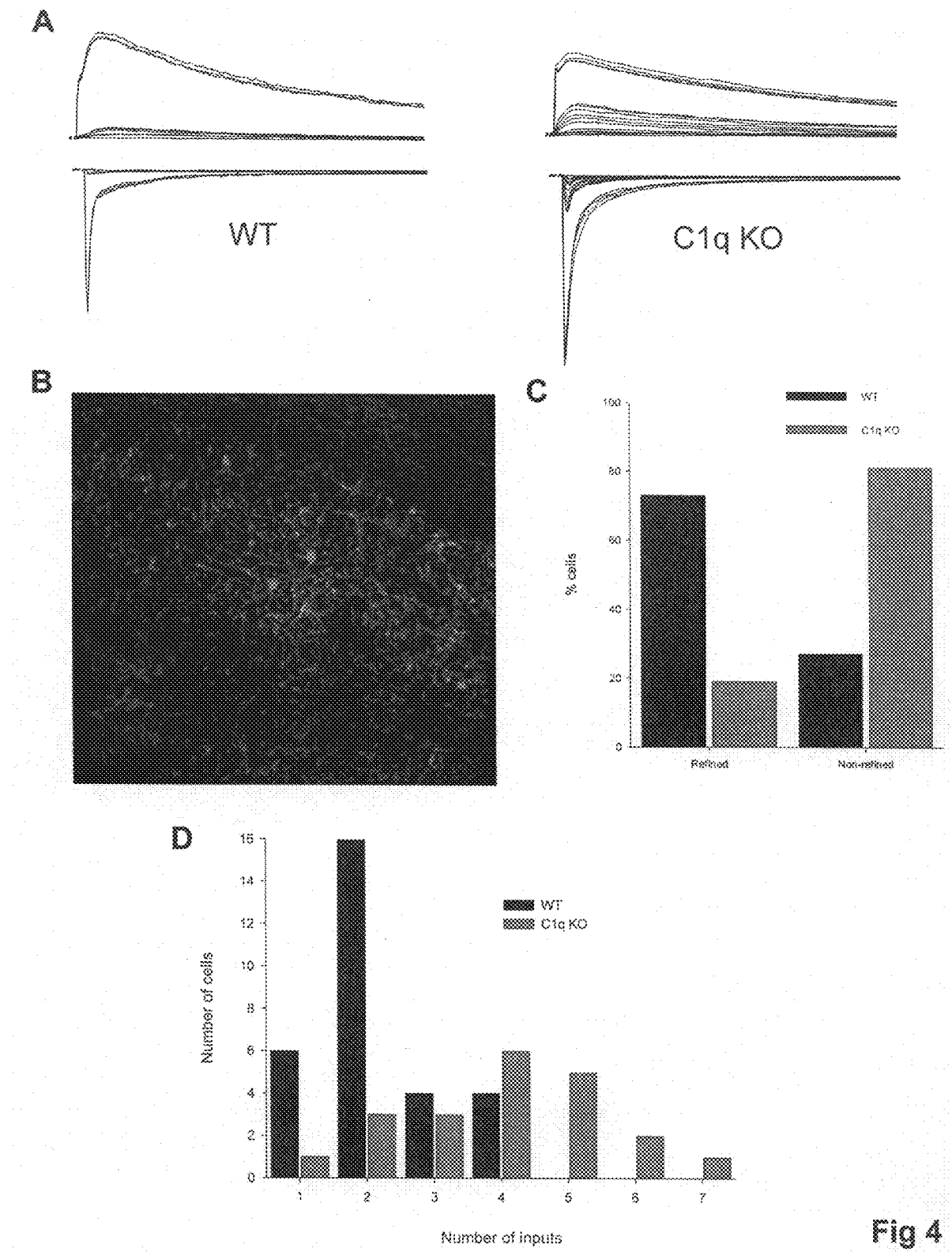
FIGS. 4A-4D. LGN neurons remain multiply-innervated in C1q-deficient mice. A. Representative traces are of single LGN neurons recorded from a WT and C1q KO mouse. Superposition of the peaks of the rapid inward current (AMPAR, −70 mV), and slower decaying outward current (NMDAR, +40 mV) represent the recruitment of individual axons. B. Recordings from LGN neurons of P30 mice in acute parasagittal brain slices. The optic tract was stimulated in small incremental intensity steps, and measured the amplitude of evoked responses in LGN neurons (red) in the contralateral region adjacent to the optic tract in C1q KOs and age matched controls. CTβ labeled contralateral retinal projections are shown in green, and ipsilateral projections are in blue. C. 81% of the cells recorded were classified as unrefined (greater than 2 inputs) compared to 27% in age matched wild type controls (C1q KO n=21, WT n=30 cells, p<0.001). D. Summary of response properties of control and C1q KO LGN neurons. C1q KOs remain multiply-innervated (average of 4±0.3 inputs, n=21) compared to age-matched WT controls (average of 2.2±0.2 inputs, n=30, p<0.001).

In order to test directly whether C1q KO fail to undergo this form of developmental synapse elimination, we studied the retinogeniculate synapses of P26-P33 C1q KO mice in acute parasagittal brain slices. We stimulated the optic tract in small incremental intensity steps, and measured the amplitude of evoked responses in LGN neurons in the contralateral region adjacent to the optic tract in C1q KOs and age matched controls (red neurons shown in FIG. 4, B). Representative traces shown in FIG. 4A are of single LGN neurons recorded from a WT and C1q KO mouse. The peaks of the rapid inward current (AMPAR, −70 mV), and slower decaying outward current (NMDAR, +40 mV) represent the recruitment of individual axons. We found that C1q KOs remain multiply-innervated (average of 4±0.3 inputs, n=21) compared to age-matched WT controls (average of 2.2±0.2 inputs, n=30, $p<0.001$). Although there was no significant difference in the maximum amplitude of AMPA or NMDA responses between C1q KO and WTs, the average amplitude of evoked responses were significantly reduced in C1q KOs (data not shown). We observed many small amplitude responses in C1q KOs (as shown in FIG. 4A) in approximately 80% of the slices obtained from C1q KO mice. As summarized in FIG. 11C, 81% of the cells recorded were classified as unrefined (greater than 2 inputs) compared to 27% in age matched wild type controls (C1q KO n=21, WT n=30 cells, $p<0.001$).

Taken together, these experiments indicate that C1q is necessary for the structural and functional elimination inappropriate synaptic connections in the developing retinogeniculate pathway.

Role of the complement cascade in developmental synapse elimination. C1q is the initiating protein of the classical complement cascade. Activated C1q undergoes a conformational change to activate a sequential cascade of downstream proteases, including the major complement protein, C3. Activated C3 fragments (C3b, iC3b) can directly opsonize dead cells and pathogens for phagocytosis, much like C1q. Alternatively, C3-activation can activate downstream complement proteins C5-C9 to eliminate unwanted cells via the formation of a membrane attack complex, which permeabilizes cell and lyses the cell.

Figure 5:
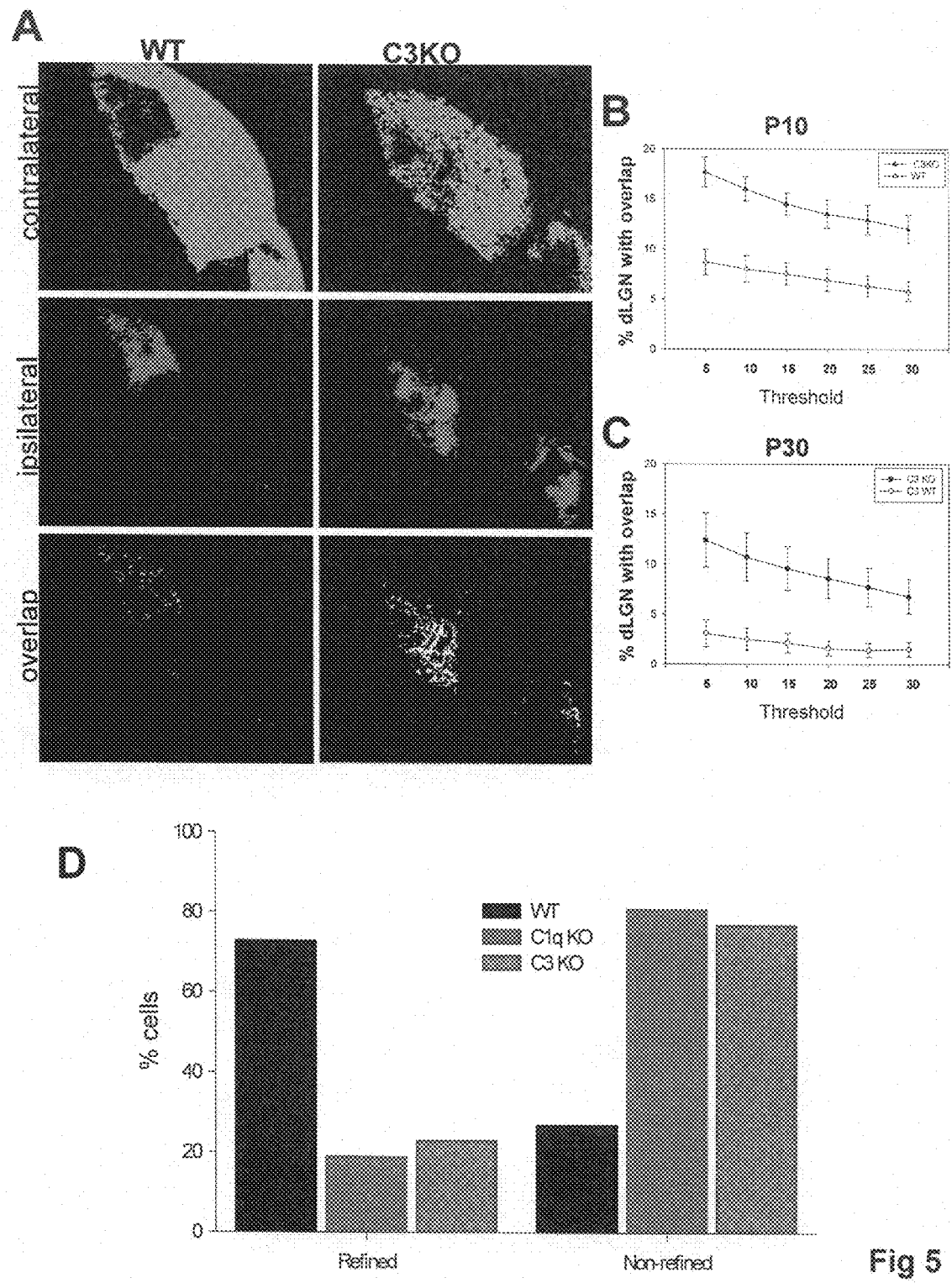
FIGS. 5A-5D. Mice deficient in C3 also have defects in synapse elimination. A. Anterograde tracing exps showing C3 KO mice at P30 exhibit significant overlap between RGC axons from left and right eyes (yellow) compared to littermate WT controls. B Quantification of the percentage of dLGN receiving overlapping inputs from the ipsilateral eye in C1q KO vs WT controls at P10 (B) and P30 (C). C1q KO mice exhibit significantly more overlap than WT mice, regardless of threshold. D. Electrophysiological recordings of P30-34 dLGN neurons indicate that LGN neurons recorded from C3 KO mice remain multi-innervated (non refined) and had similar response properties to C1q KO mice.

To determine whether C3 is necessary for synapse elimination, we obtained mice deficient in complement protein C3 to investigate whether absence of C3 mimics the phenotype we observed in the LGNs of C1q-deficient mice. We performed similar anterograde tracing experiments and electrophysiological recording of retino-geniculate synapses in C3KO mice and age matched controls as described above. Consistent with our hypothesis, C3 KO mice have defects in LGN segregation and synapse elimination that closely mimic the C1qKO phenotype. C3 KO mice had significant defects in eye-specific segregation, both at P10 and P30 (FIG. 5A-C). Quantification of the percentage of dLGN occupied by overlapping retinal axons from both eyes indicate that C3KO mice had significantly more overlap than age matched and littermate controls. Electrophysiological recordings of P30-34 dLGN neurons indicate that LGN neurons recorded from C3 KO mice remain multi-innervated and had similar response properties to C1q KO mice (FIG. 5D). Together, these findings provide supporting evidence that the classical complement cascade mediates normal developmental synapse elimination.

Figure 6:
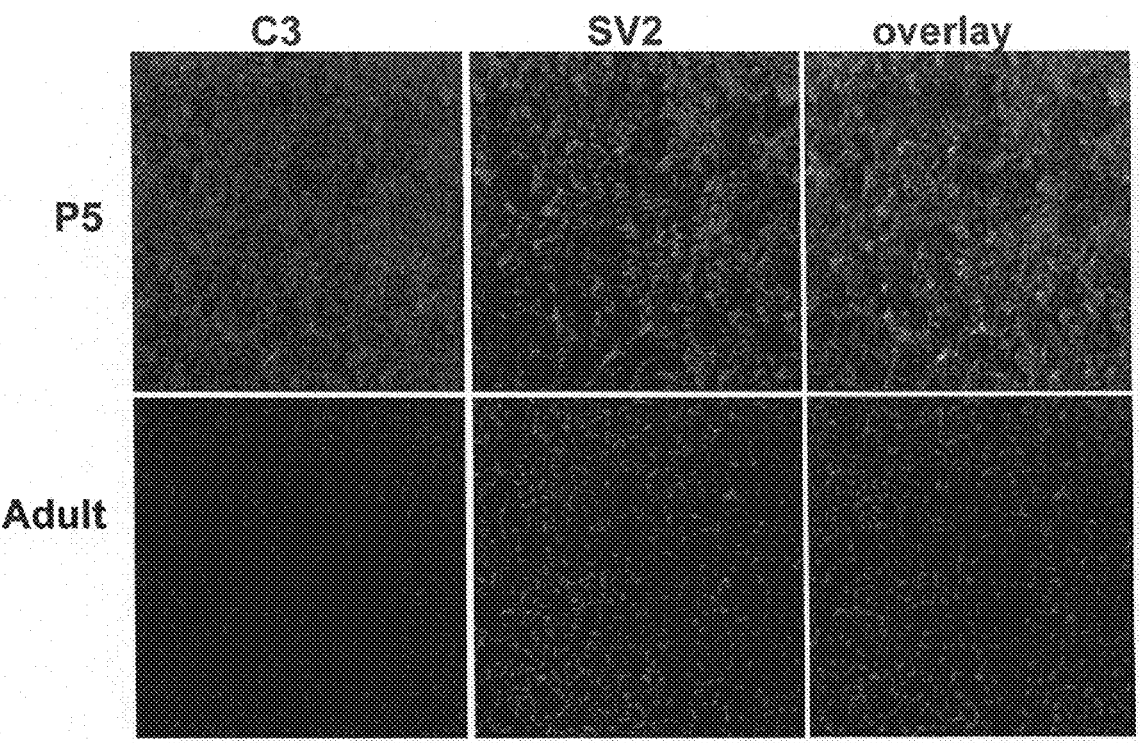
FIGS. 6A-6B. Complement C3 is expressed at developing CNS synapses. A Double immunohistochemistry with the synaptic antibody SV2, revealed that many C3-positive puncta co-localized with synaptic puncta in the developing (P5), but not the adult brain (P60). B. Western blot analysis of protein lysates prepared from perfused, developing cortex. A clear band for iC3b (43 kD) was observed in postnatal cortex, and C3b levels were significantly down-regulated by P30.
Figure 6:
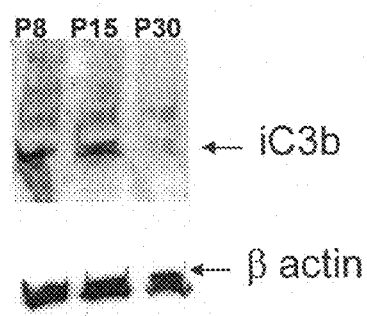

Complement C3 is expressed at developing CNS synapses. Is C3 activated and localized to synapses in the postnatal brain? Complement activation has been shown to occur in the brain after injury, stroke, and inflammation, but the expression and localization during normal postnatal development has not been previously examined. We performed immunostaining experiments in cryosections of perfused postnatal mouse and rat brain using polyclonal antibodies against rat C3. We found that C3 protein is expressed in postnatal rodent brain and cortex, but C3 protein was not detected in the adult brain (FIG. 6A). Importantly, double immunohistochemistry with the synaptic antibody SV2, revealed that many C3-positive puncta co-localized with synaptic puncta (FIG. 6A). Immunoreactivity was specific for C3, as C3-specific antibodies failed to stain brain sections prepared from C3-deficient mice.

Figure 7:
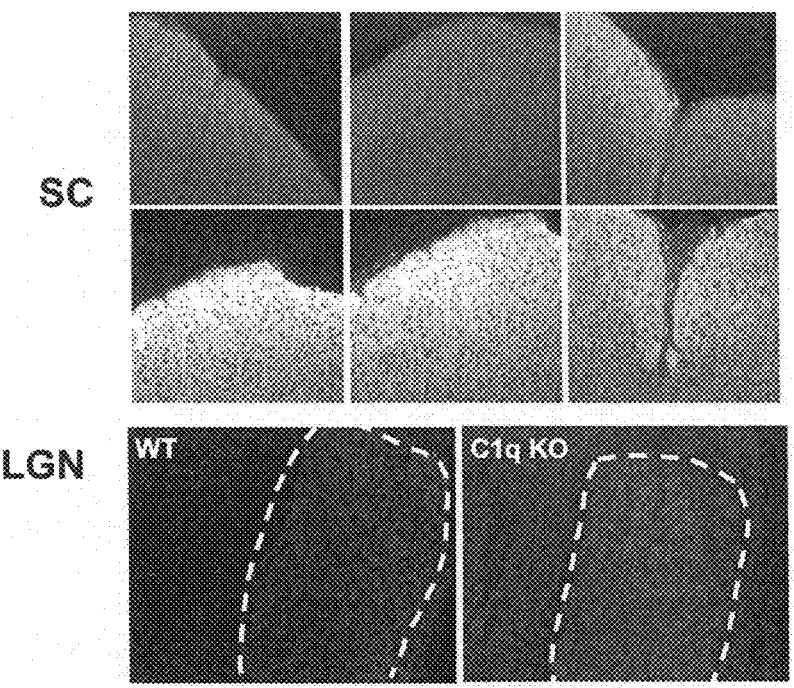
FIGS. 7A-7B. Complement-deficient mice have more synapses. A. Immunohistochemistry of pre-synaptic protein, vGLUT2 in the superior colliculi (SC) and dLGN of P16 C1q KO and control mice indicate an increase in average intensity of staining in C1q KOs. Sections were processed and immunostained in parallel and all images were collected at identical cameral exposures. B. High resolution confocal microscopy imaging revealed a higher density of postsynaptic PSD95 puncta (green) in dLGNs of P16 C1q KO mice compared to littermate controls.
Figure 7:
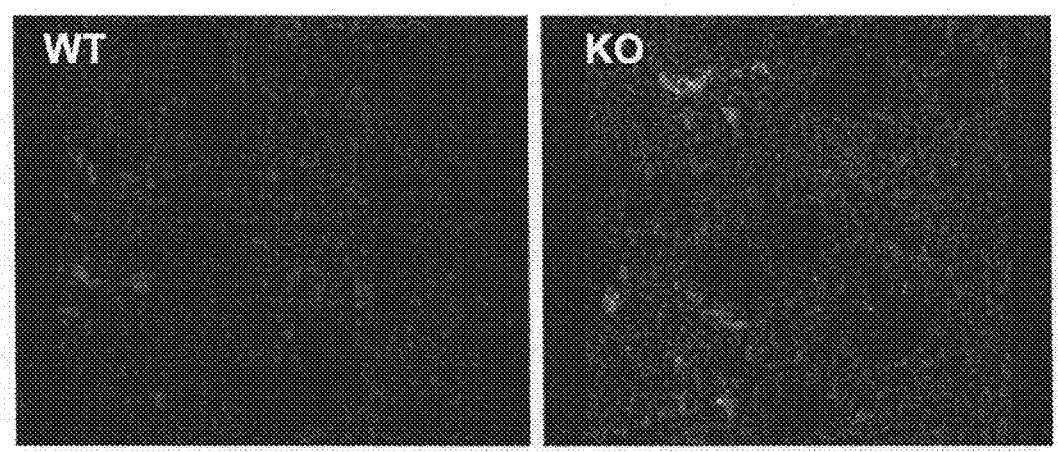

Western blot analysis of protein lysates prepared from perfused, developing cortex provide direct evidence that C3 is activated in the developing brain (FIG. 7B). When native C3 is cleaved, activated C3 fragments (43 kD) can be detected by SDS-PAGE and western blot analyses using polyclonal antibodies against C3. As shown in FIG. 7B, we observed a clear band for iC3b in postnatal cortex, and C3b levels were significantly down-regulated by P30. Together these data provide evidence that the complement cascade is activated during the period of synaptic pruning in the brain.

Figure 8:
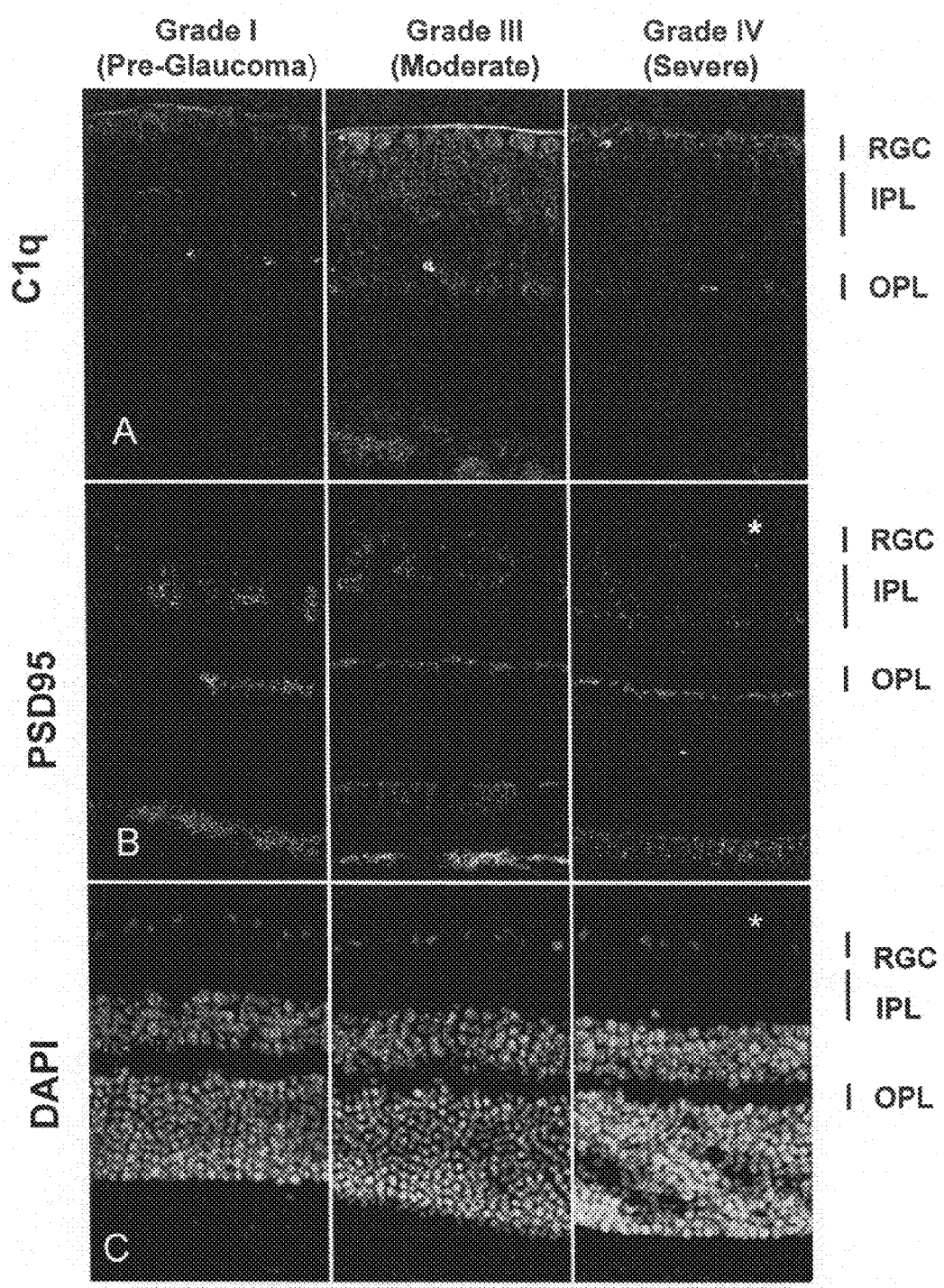
FIG. 8. C1q is localized to synapse in early stages of glaucoma. Immunohistochemistry of A. C1q and the postsynaptic protein, B. PSD95 in the RGC and C. synaptic layers of retinas from DBA/2J mice various stages of disease (preglaucoma, early, moderate and late stage). Punctate C1q immunoreactivity (top row) in the IPL of retinas from DBA/2J mice with moderate (Grade III, 6-12 months) glaucoma and before significant RGC or synapse cell loss C1q staining is present in the IPL, but less pronounced in retinas collected from retinas with severe glaucoma and RGC death (as seen in DAPI staining of RGC cell bodies, bottom row).

Complement-deficient mice have more synapses. An increase in synapse number would provide further evidence that complement proteins are required for synapse elimination. To address this question, we compared the relative intensity of synaptic staining the LGNs and superior colliculi of C1q KO mice and littermate controls using several synaptic antibodies including vGLUT2, a vesicular glutamate transporter that is selectively expressed by retinal ganglion cells. As shown in FIG. 8, we found a general increase in the intensity of vGLUT2 staining in both the superior colliculi (SC) and dLGN of C1q KO mice (FIG. 8A, B). Sections from P16 C1qKO and controls were processed and immunostained in parallel, and all images were collected at identical cameral exposures. In addition, high resolution confocal microscopy imaging revealed a higher density of PSD95 puncta in dLGNs of P16 C1q KO mice compared to littermate controls. (FIG. 8C).

C1q is localized to synapses in early stages of neurodegenerative disease. Could synapse loss at early stages of neurodegenerative disease involve a re-activation of developmental synapse elimination mediated by the complement cascade? Complement expression and activation are known to be significantly enhanced following brain injury and in various neurodegenerative diseases, such as Alzheimer's Disease (AD). In many cases, astrocytes, and microglia become reactive and could therefore re-express the signal that induces C1q expression in developing neurons. For example, AD is caused by a massive degeneration of synapses, and it has become increasingly clear that synapse loss occurs long before neuropathology and clinical symptoms in AD brains. C1q protein is 10- to 80-fold up-regulated in AD brain, and amyloid β-peptide (Aβ) is a powerful activator of C1q.

We investigated this question using a well characterized mouse model of glaucoma. The glaucomas are neurodegenerative diseases involving death of retinal ganglion cells and optic nerve head excavation that is often associated with elevated intraocular pressure (IOP). DBA/2J mice have been shown to exhibit an age-related progressive glaucoma. The period when mice have elevated IOP extends from 6 months to 16 months, with 8-9 months representing an important transition to high IOP for many mice. Optic nerve degeneration follows IOP elevation, with the majority of optic nerves being severely damaged by 12 months of age.

Could C1q-dependent synapse elimination trigger synaptic loss before RGC death and neurodegeneration? To address this question, we looked at the timing and localization of C1q immunoreactivity in the RGC and synaptic layers of retinas of DBA/2J and control mice at various stages of disease (pre-glaucoma, early, moderate and late stage). As shown in FIG. 15, we found punctate C1q immunoreactivity in the IPL of retinas from DBA/2J mice with moderate (Grade III, 6-12 months) glaucoma. At this stage, there is no significant RGC or synapse cell loss, as indicated by PSD-95 staining in the IPL. C1q staining is present in the IPL, but less pronounced in retinas collected from retinas with severe glaucoma (Severe, 9-12 months). At this stage there is significant RGC and death and degeneration of retinal axons. Importantly, C1q immunoreactivity was not observed in the IPL of young DBA mice (1-2 months), or in retinas obtained from a control strain (2-12 months of age) that lacked the glaucoma gene. Together our findings indicate that C1q is localized to synapses in the IPL before significant synapse loss and RGC death, which supports the notion that complement is mediating synapse loss in early stages of disease.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of maintaining neuronal function in a patient with glaucoma, comprising the step of: administering a therapeutic amount of C1 inhibitor protein to a patient suffering from glaucoma to maintain neuronal function.

* * * * *

UNITED STATES PATENT AND TRADEMARK OFFICE
CERTIFICATE OF CORRECTION

PATENT NO.         : 8,148,330 B2
APPLICATION NO.    : 11/636001
DATED              : April 3, 2012
INVENTOR(S)        : Barres et al.

Page 1 of 1

It is certified that error appears in the above-identified patent and that said Letters Patent is hereby corrected as shown below:

Replace Column 1, lines 4-9 with:

-- FEDERALLY-SPONSORED RESEARCH OR DEVELOPMENT
This invention was made with Government support under contracts DA015043 and EY011310 awarded by the National Institutes of Health. The Government has certain rights in this invention. --

Signed and Sealed this
Third Day of July, 2012

David J. Kappos
*Director of the United States Patent and Trademark Office*